United States Patent
Haisma et al.

(10) Patent No.: US 10,370,660 B2
(45) Date of Patent: Aug. 6, 2019

(54) ANTISENSE OLIGONUCLEOTIDES TO TREAT DYSTROPHIC EPIDERMOLYSIS BULLOSA

(71) Applicant: ProQR Therapeutics II B.V., Leiden (NL)

(72) Inventors: Elisabeth Marlene Haisma, Leiden (NL); Marko Potman, Leiden (NL); Gerardus Johannes Platenburg, Leiden (NL)

(73) Assignee: WINGS THERAPEUTICS, INC., Berkeley, CA (US)

( * ) Notice: Subject to any disclaimer, the term of this patent is extended or adjusted under 35 U.S.C. 154(b) by 0 days.

(21) Appl. No.: 15/575,559

(22) PCT Filed: May 20, 2016

(86) PCT No.: PCT/EP2016/061495
§ 371 (c)(1),
(2) Date: Nov. 20, 2017

(87) PCT Pub. No.: WO2016/185041
PCT Pub. Date: Nov. 24, 2016

(65) Prior Publication Data
US 2018/0245078 A1 Aug. 30, 2018

(30) Foreign Application Priority Data

May 21, 2015 (GB) .................................. 1508733.1
Sep. 17, 2015 (GB) .................................. 1516505.3

(51) Int. Cl.
| | |
|---|---|
| *A61K 48/00* | (2006.01) |
| *C07H 21/02* | (2006.01) |
| *C07H 21/04* | (2006.01) |
| *C12N 15/113* | (2010.01) |

(52) U.S. Cl.
CPC ........ *C12N 15/113* (2013.01); *C12N 2310/11* (2013.01); *C12N 2310/321* (2013.01); *C12N 2320/32* (2013.01)

(58) Field of Classification Search
CPC .... C12N 15/113; C12N 15/111; A61K 31/713
See application file for complete search history.

(56) References Cited

U.S. PATENT DOCUMENTS

| 5,139,941 A | 8/1992 | Muzyczka et al. |
|---|---|---|
| 5,801,154 A * | 9/1998 | Baracchini ............. C07H 21/00 435/325 |
| 6,531,456 B1 | 3/2003 | Kurtzman et al. |

FOREIGN PATENT DOCUMENTS

| WO | WO 2013/053819 A1 * | 4/2013 | ........... C12N 15/113 |
|---|---|---|---|
| WO | WO-2013053819 A1 | 4/2013 | |
| WO | WO-20140150074 A1 | 9/2014 | |
| WO | WO-2016196670 A1 | 12/2016 | |
| WO | WO-2016202779 A1 | 12/2016 | |

OTHER PUBLICATIONS

Aartsma-Rus and van Ommen (2007) "Antisense-mediated exon skipping: A versatile tool with therapeutic and research applications," RNA, 13(10):1609-24.
Chen et al. (2002) "Restoration of type VII collagen expression and function in dystrophic epidermolysis bullosa," Nat Genet., 32(4):670-5.
Chiorini et al. (1999) "Cloning and characterization of adeno-associated virus type 5," J. of Virology, 73(2):1309-19.
Dorn et al. (2008) "Clinical application of CpG-, non-CpG-, and antisense oligodeoxynucleotides as immunomodulators," Curr. Opin. Mol. Ther., 10(1):10-20.
Egholm et al. (1993) "PNA hybridizes to complementary oligo-nucleotides obeying the Watson-Crick hydrogen-bonding rules," Nature, 365(6446):566-8.
Fine et al. (2014) "Inherited epidermolysis bullosa: Updated recommendations on diagnosis and classification," J. Am. Acad. Dermatol., 70(6):1103-26.
Gorman et al. (1998) "Stable alteration of pre-mRNA splicing patterns by modified U7 small nuclear RNAs," Proc. Natl. Acad. Sci. USA, 95(9):4929-34.
Goto et al. (2006) "Targeted Skipping of a Single Exon Harboring a Premature Termination Codon Mutation: Implications and Potential for Gene Correction Therapy for Selective Dystrophic Epidermolysis Bullosa Patients," J. Invest. Dermatol., 126(12):2614-20.
Govindaraju et al. (2005) "Backbone-extended pyrrolidine peptide nucleic acids (bepPNA): design, synthesis and DNA/RNA binding studies," Chem. Commun. (Camb), (4):495-7.
International Search Report for PCT/EP2016/061495, dated Oct. 12, 2016 (7 pages).
Keswani et al. (2012) "Pseudotyped adeno-associated viral vector tropism and transduction efficiencies in murine wound healing," Wound Repair Regen., 20(4):592-600.
Mecklenbeck et al. (2002) "A microinjected COL7A1-PAC vector restores synthesis of intact procollagen VII in a dystrophic epidermolysis bullosa keratinocyte cell line," Hum. Gen Ther., 13(13):1655-62.

(Continued)

*Primary Examiner* — Amy H Bowman
(74) *Attorney, Agent, or Firm* — Mintz Levin Cohn Ferris Glovsky and Popeo PC

(57) ABSTRACT

An antisense oligonucleotide capable of preventing or reducing exon 80 inclusion into a human COL7A1 mRNA, and methods for preventing or reducing exon 80 inclusion into a human COL7A1 mRNA.

20 Claims, 6 Drawing Sheets

Specification includes a Sequence Listing.

(56) References Cited

OTHER PUBLICATIONS

Morita et al. (2001) "2'-O,4'-C-Ethylene-bridged nucleic acids (ENA) with nuclease resistance and high affinity for RNA," Nucleic Acids Res. Suppl., (1):241-242.
Nielsen et al. (1991) "Sequence-selective recognition of DNA by strand displacement with a thymine-substituted polyamide," Science, 254(5037):1497-500.
Suter et al. (1999) "Double-target antisense U7 snRNAs promote efficient skipping of an aberrant exon in three human beta-thalassemic mutations," Hum. Mol. Genet., 8(13):2415-23.
Titeux et al. (2010) "SIN retroviral vectors expressing COL7A1 under human promoters for ex vivo gene therapy of recessive dystrophic epidermolysis bullosa," Mol. Ther., 18(8):1509-18.
Turczynski et al. (2012) "Antisense-mediated exon skipping to reframe transcripts," Methods Mol Biol., 867:221-38.
Written Opinion for PCT/EP2016/061495, dated Oct. 12, 2016 (10 pages).

\* cited by examiner

FIGURE 1

```
                                                                                                              Name            SEQ ID NO:
aacaggcccaagtgaggcccagattgaggctcatcagtgccctctctatgtagGGTCTGCAGGGTCCAAGAGGCCCCCTGGCCCAGTGgtgagtacccaagaacttcacctgtcttgcc-3'         1
aacaggcccaagtgaggcccagattgaggctcatcagtgccctctctatgtag-3'                                                                          19
                                 GGTCTGCAGGGTCCAAGAGGCCCCCTGGCCCAGTG-3'                                                           18
                                                        gtgagtacccaagaacttcacctgtcttgcc-3'                                         20
                                                        CCTGGCCCAGTGgtgagtacccaa-3'                                                21

AONs ucCCAGAGACGUCCCAGGUUCUCCGG-5'                                      ESE80.3                  2
ucCCAGAGACAUCCCAGGUUCUCCGG-5'                                      ESE80.3-Q2I70X           3
gagauacaucCCAGACGUCC-5'                                            AON80.1                  4
aucCCAGAGACGUCCCAGGUUC-5'                                          AON80.2                  5
           GACGUCCCAGGUUCUCCGGG-5'                                 AON80.3                  6
                  GGACCGGGUCACcacucaugggu u-5'                     AON80.4                  7
                  GGACCGGGUCACcacucaugg-5'                         AON80.5                  8
                  GGGACCGGGUCACcacucaug-5'                         AON80.5.1               25
                  GGGGACCGGGUCACcacucau-5'                         AON80.5.2               26
                   GACCGGGUCACcacucaugg-5'                         AON80.5.3               27
                   ACCGGGUCACcacucauggu-5'                         AON80.5.4               28
                    CCGGGUCACcacucaugggu u-5'                      AON80.5.5               29
                  GGACCGGGUCACcacucaug-5'                          AON80.5.7               31
                   GACCGGGUCACcacucaugg-5'                         AON80.5.8               32
CCAGAGACGUCCCAGGUUCUCCGGGGGGACCGGGUCAC-5'                          AON80.13                30
                                 UCACcacu-5'                                               22
                                 GGUCACca-5'                                               23
                                     ACcacuca-5'                                           24
                                              gguucuuggaagugqacagaacgg-5'                   9
```

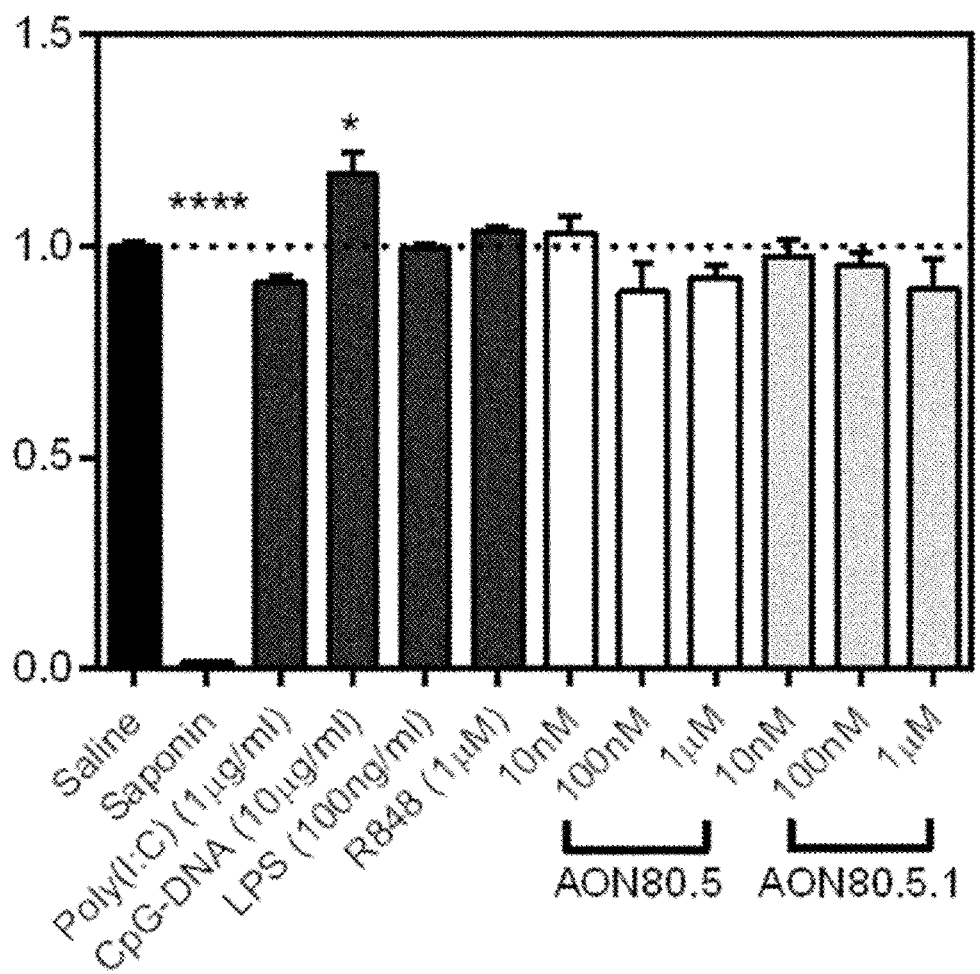

SEQUENCE LISTING

<160> NUMBER OF SEQ ID NOS: 33

<210> SEQ ID NO 1
<211> LENGTH: 121
<212> TYPE: DNA
<213> ORGANISM: Homo sapiens
<220> FEATURE:
<223> OTHER INFORMATION: COL7A1 gene

<400> SEQUENCE: 1
aacaggccca agtgaggccc agattgaggc tcatcagtgc cctctctatg tagggtctgc      60
agggtccaag aggccccct ggcccagtgg tgagtaccca agaaccttca cctgtcttgc      120
c                                                                    121

<210> SEQ ID NO 2
<211> LENGTH: 24
<212> TYPE: RNA
<213> ORGANISM: Artificial Sequence
<220> FEATURE:
<223> OTHER INFORMATION: Description of Artificial Sequence: Synthetic
      antisense oligonucleotide

<400> SEQUENCE: 2
ggccucuugg acccugcaga cccu                                            24

<210> SEQ ID NO 3
<211> LENGTH: 24
<212> TYPE: RNA
<213> ORGANISM: Artificial Sequence
<220> FEATURE:
<223> OTHER INFORMATION: Description of Artificial Sequence: Synthetic
      antisense oligonucleotide

<400> SEQUENCE: 3
ggccucuugg acccuacaga cccu                                            24

<210> SEQ ID NO 4
<211> LENGTH: 20
<212> TYPE: RNA
<213> ORGANISM: Artificial Sequence
<220> FEATURE:
<223> OTHER INFORMATION: Description of Artificial Sequence: Synthetic
      antisense oligonucleotide

<400> SEQUENCE: 4
ccugcagacc cuacauagag                                                 20

<210> SEQ ID NO 5
<211> LENGTH: 20
<212> TYPE: RNA
<213> ORGANISM: Artificial Sequence
<220> FEATURE:
<223> OTHER INFORMATION: Description of Artificial Sequence: Synthetic
      antisense oligonucleotide

<400> SEQUENCE: 5
cuuggacccu gcagacccua                                                 20

<210> SEQ ID NO 6
<211> LENGTH: 20
<212> TYPE: RNA
<213> ORGANISM: Artificial Sequence
<220> FEATURE:
<223> OTHER INFORMATION: Description of Artificial Sequence: Synthetic
      antisense oligonucleotide

```
<400> SEQUENCE: 6
gggccucuug gacccugcag                                              20

<210> SEQ ID NO 7
<211> LENGTH: 24
<212> TYPE: RNA
<213> ORGANISM: Artificial Sequence
<220> FEATURE:
<223> OTHER INFORMATION: Description of Artificial Sequence: Synthetic
      antisense oligonucleotide

<400> SEQUENCE: 7
uuggguacuc accacugggc cagg                                         24

<210> SEQ ID NO 8
<211> LENGTH: 21
<212> TYPE: RNA
<213> ORGANISM: Artificial Sequence
<220> FEATURE:
<223> OTHER INFORMATION: Description of Artificial Sequence: Synthetic
      antisense oligonucleotide

<400> SEQUENCE: 8
gguacucacc acugggccag g                                            21

<210> SEQ ID NO 9
<211> LENGTH: 24
<212> TYPE: RNA
<213> ORGANISM: Artificial Sequence
<220> FEATURE:
<223> OTHER INFORMATION: Description of Artificial Sequence: Synthetic
      antisense oligonucleotide

<400> SEQUENCE: 9
ggcaagacag gugaagguuc uugg                                         24

<210> SEQ ID NO 10
<211> LENGTH: 25
<212> TYPE: RNA
<213> ORGANISM: Artificial Sequence
<220> FEATURE:
<223> OTHER INFORMATION: Description of Artificial Sequence: Synthetic
      antisense oligonucleotide

<400> SEQUENCE: 10
cagggcacag gaugggggca agaca                                        25

<210> SEQ ID NO 11
<211> LENGTH: 25
<212> TYPE: RNA
<213> ORGANISM: Artificial Sequence
<220> FEATURE:
<223> OTHER INFORMATION: Description of Artificial Sequence: Synthetic
      antisense oligonucleotide

<400> SEQUENCE: 11
gucacugggg cagggcacag gaugg                                        25

<210> SEQ ID NO 12
<211> LENGTH: 25
<212> TYPE: RNA
<213> ORGANISM: Artificial Sequence
<220> FEATURE:
<223> OTHER INFORMATION: Description of Artificial Sequence: Synthetic
      antisense oligonucleotide

<400> SEQUENCE: 12
```

```
cuugggccug uucccaacccu cuggg                                          25

<210> SEQ ID NO 13
<211> LENGTH: 22
<212> TYPE: RNA
<213> ORGANISM: Artificial Sequence
<220> FEATURE:
<223> OTHER INFORMATION: Description of Artificial Sequence: Synthetic
      antisense oligonucleotide

<400> SEQUENCE: 13
aucugggccu cacuugggcc ug                                              22

<210> SEQ ID NO 14
<211> LENGTH: 25
<212> TYPE: RNA
<213> ORGANISM: Artificial Sequence
<220> FEATURE:
<223> OTHER INFORMATION: Description of Artificial Sequence: Synthetic
      antisense oligonucleotide

<400> SEQUENCE: 14
agggcacuga ugagccucaa ucugg                                           25

<210> SEQ ID NO 15
<211> LENGTH: 25
<212> TYPE: RNA
<213> ORGANISM: Artificial Sequence
<220> FEATURE:
<223> OTHER INFORMATION: Description of Artificial Sequence: Synthetic
      antisense oligonucleotide

<400> SEQUENCE: 15
cauagagagg gcacugauga gccuc                                           25

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
caaggtccca aaggagacag                                                 20

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
agtcccacag ctccagtagg                                                 20

<210> SEQ ID NO 18
<211> LENGTH: 36
<212> TYPE: DNA
<213> ORGANISM: Homo sapiens
<220> FEATURE:
<223> OTHER INFORMATION: COL7A1 gene

<400> SEQUENCE: 18
ggtctgcagg gtccaagagg ccccccctggc ccagtg                              36
```

<210> SEQ ID NO 19
<211> LENGTH: 53
<212> TYPE: DNA
<213> ORGANISM: Homo sapiens
<220> FEATURE:
<223> OTHER INFORMATION: COL7A1 gene

<400> SEQUENCE: 19
aacaggccca agtgaggccc agattgaggc tcatcagtgc cctctctatg tag        53

<210> SEQ ID NO 20
<211> LENGTH: 32
<212> TYPE: DNA
<213> ORGANISM: Homo sapiens
<220> FEATURE:
<223> OTHER INFORMATION: COL7A1 gene

<400> SEQUENCE: 20
gtgagtaccc aagaaccttc acctgtcttg cc                                32

<210> SEQ ID NO 21
<211> LENGTH: 24
<212> TYPE: DNA
<213> ORGANISM: Homo sapiens
<220> FEATURE:
<223> OTHER INFORMATION: COL7A1 gene

<400> SEQUENCE: 21
cctggcccag tggtgagtac ccaa                                         24

<210> SEQ ID NO 22
<211> LENGTH: 8
<212> TYPE: RNA
<213> ORGANISM: Artificial Sequence
<220> FEATURE:
<223> OTHER INFORMATION: Description of Artificial Sequence: Synthetic
      antisense oligonucleotide

<400> SEQUENCE: 22 ucaccacu                                                           8

<210> SEQ ID NO 23
<211> LENGTH: 8
<212> TYPE: RNA
<213> ORGANISM: Artificial Sequence
<220> FEATURE:
<223> OTHER INFORMATION: Description of Artificial Sequence: Synthetic
      antisense oligonucleotide

<400> SEQUENCE: 23 accacugg                                                           8

<210> SEQ ID NO 24
<211> LENGTH: 8
<212> TYPE: RNA
<213> ORGANISM: Artificial Sequence
<220> FEATURE:
<223> OTHER INFORMATION: Description of Artificial Sequence: Synthetic
      antisense oligonucleotide

<400> SEQUENCE: 24 acucacca                                                           8

<210> SEQ ID NO 25
<211> LENGTH: 21

```
<212> TYPE: RNA
<213> ORGANISM: Artificial Sequence
<220> FEATURE:
<223> OTHER INFORMATION: Description of Artificial Sequence: Synthetic
      antisense oligonucleotide

<400> SEQUENCE: 25
guacucacca cugggccagg g                                                    21

<210> SEQ ID NO 26
<211> LENGTH: 21
<212> TYPE: RNA
<213> ORGANISM: Artificial Sequence
<220> FEATURE:
<223> OTHER INFORMATION: Description of Artificial Sequence: Synthetic
      antisense oligonucleotide

<400> SEQUENCE: 26
uacucaccac ugggccaggg g                                                    21

<210> SEQ ID NO 27
<211> LENGTH: 21
<212> TYPE: RNA
<213> ORGANISM: Artificial Sequence
<220> FEATURE:
<223> OTHER INFORMATION: Description of Artificial Sequence: Synthetic
      antisense oligonucleotide

<400> SEQUENCE: 27
ggguacucac cacugggcca g                                                    21

<210> SEQ ID NO 28
<211> LENGTH: 21
<212> TYPE: RNA
<213> ORGANISM: Artificial Sequence
<220> FEATURE:
<223> OTHER INFORMATION: Description of Artificial Sequence: Synthetic
      antisense oligonucleotide

<400> SEQUENCE: 28
uggguacuca ccacugggcc a                                                    21

<210> SEQ ID NO 29
<211> LENGTH: 21
<212> TYPE: RNA
<213> ORGANISM: Artificial Sequence
<220> FEATURE:
<223> OTHER INFORMATION: Description of Artificial Sequence: Synthetic
      antisense oligonucleotide

<400> SEQUENCE: 29
uuggguacuc accacugggc c                                                    21

<210> SEQ ID NO 30
<211> LENGTH: 36
<212> TYPE: RNA
<213> ORGANISM: Artificial Sequence
<220> FEATURE:
<223> OTHER INFORMATION: Description of Artificial Sequence: Synthetic
      antisense oligonucleotide

<400> SEQUENCE: 30
cacugggcca ggggggccuc uuggacccug cagacc                                    36

<210> SEQ ID NO 31
<211> LENGTH: 20
<212> TYPE: RNA
```

```
<213> ORGANISM: Artificial Sequence
<220> FEATURE:
<223> OTHER INFORMATION: Description of Artificial Sequence: Synthetic
      antisense oligonucleotide

<400> SEQUENCE: 31
guacucacca cugggccagg                                                   20

<210> SEQ ID NO 32
<211> LENGTH: 20
<212> TYPE: RNA
<213> ORGANISM: Artificial Sequence
<220> FEATURE:
<223> OTHER INFORMATION: Description of Artificial Sequence: Synthetic
      antisense oligonucleotide

<400> SEQUENCE: 32
gguacucacc acugggccag                                                   20

<210> SEQ ID NO 33
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
gaagggggag cctggaga                                                     18
```

ANTISENSE OLIGONUCLEOTIDES TO TREAT DYSTROPHIC EPIDERMOLYSIS BULLOSA

RELATED APPLICATIONS

This application is a § 371 National Stage Application of PCT/EP2016/061495, filed May 20, 2016, which claims priority to and the benefit of United Kingdom patent application no. 1508733.1, filed May 21, 2015, and United Kingdom patent application no. 1516505.3, filed Sep. 17, 2015, the entire disclosures of each of which are incorporated herein by reference for all purposes.

SEQUENCE LISTING

The instant application contains a Sequence Listing which has been submitted in ASCII format via EFS-Web and is hereby incorporated by reference in its entirety. The ASCII copy, created on Feb. 12, 2018, is named PQR-008_SL.txt and is 8,194 bytes in size.

FIELD OF THE INVENTION

The present invention is concerned with oligonucleotides suitable for use in treating human disease. More in particular the present invention is concerned with antisense oligonucleotides (AONs) suitable for the treatment of dystrophic epidermolysis bullosa.

Disease Background

Epidermolysis Bullosa (EB) is a group of heritable skin diseases, which are characterized by chronic fragility and blistering of the skin and mucous membranes. Depending on the subtype, the spectrum of symptoms of the EB is very broad, ranging from minimal skin fragility to very severe symptoms with general complications. Worldwide about 350,000 patients are affected. In some forms of EB, also nails, hair and teeth may be involved. The main types of EB include EB Simplex (EBS), Junctional EB (JEB), Dystrophic EB (DEB) and Kindler syndrome (KS) (Fine et al. 2014).

DEB affects about 25% of EB patients, can be either dominantly or recessively inherited, and involves defects in Type VII collagen (COL7A1, OMIM 120120). COL7A1 encodes the alpha-1 chain of collagen VII. Collagen VII functions as an anchoring fibril of the upper part of the dermis to the lamina densa (part of the basement membrane). Following post-translational modification three identical alpha-1 chains fold together with their collagenous triple helix domain. Subsequently, antiparallel dimers are formed that align to form the anchoring fibrils. Collagen VII is synthesized in the skin by keratinocytes and dermal fibroblasts. DEB disease severity roughly correlates with the amount of type VII collagen expression at the basement membrane zone.

Characteristics of Dominant Dystrophic EB (DDEB) include blistering that may be localized to the hands, feet, elbows and knees or generalized. Common findings include scarring, milia, mucous membrane involvement, and abnormal or absent nails. Recessive Dystrophic EB (RDEB, approximately 50% of DEB patients) is typically more generalized and severe than DDEB. In addition to the symptoms of DDEB, other common manifestations of RDEB include malnutrition, anemia, osteoporosis, esophageal strictures, growth retardation, webbing, or fusion of the fingers and toes causing mitten deformity (pseudosyndactyly), development of muscle contractures, malformation of teeth, microstomia and scarring of the eye. The risk of squamous cell carcinoma is greatly increased in this group as well as death from metastatic squamous cell carcinoma.

Within the gene COL7A1 more than 400 different mutations are known. One of the most prevalent affected exons (7% of RDEB) is exon 80 with more than 3 different mutations, missense mutations or mutations leading to premature termination codons (PTCs). Due to the fact that the majority of the exons of the COL7A1 gene are in frame, exon skipping is potentially a viable strategy to get rid of exons with PTC mutations, while retaining protein function (Goto et al. 2006).

Currently there is no treatment for DEB, and only palliative care is performed. Severe forms of RDEB impose a high cost on society's healthcare budget: the average costs of dressings and medication is about €200,000 per patient per year. The expected life span for DEB patients is somewhere between 30 and 40 years.

WO2013/053819 of Institut National de la Sante et de la Recherche Médicale (INSERM) discloses two 24mer antisense oligonucleotides with 22 nucleotides that are complementary to exon 80 and 2 nucleotides that are complementary to the upstream intron, which cause the entire exon to be skipped from the mRNA (see also FIG. 1):

```
ESE80.3
                                    (SEQ ID NO: 2)
GGCC UCUU GGAC CCUG CAGA CCCU

ESE80.3-Q2I70X
                                    (SEQ ID NO: 3)
GGCC UCUU GGAC CCUA CAGA CCCU
```

The exon-80-deficient mRNA most probably translates into a functional polypeptide that, although being shorter than the wild-type protein, behaves similarly to wild-type collagen VII. The inventors of the present invention tested the oligonucleotides disclosed in WO2013/053819 in human primary fibroblasts (HPF) and HeLa cells, to assess their skipping efficiency. It appears that both AONs, under the conditions tested, exhibit a skipping efficiency of less than 50%, while ESE80.3 performs slightly better than ESE80.3-Q2170X. Although these exon skipping oligonucleotides provide a promising first step in tackling this terrible disease, there is clearly still a need for further alternative oligonucleotides to improve the efficiency of exon 80 skipping.

SUMMARY OF THE INVENTION

The invention provides various AONs which are capable of preventing or reducing exon 80 inclusion into a human COL7A1 mRNA, when said mRNA is produced by splicing from a pre-mRNA in a mammalian cell (such as in a human cell in vivo). In a first aspect, the oligonucleotide (a) comprises a nucleotide sequence which is complementary to part of exon 80 and (b) is less than 24 nucleotides in length. These oligonucleotides are thus advantageously shorter than those disclosed in the prior art.

In a second aspect, the oligonucleotide comprises a nucleotide sequence which is complementary to a 3' part of exon 80 and a 5' part of the downstream intron. AONs which span the boundary between exon 80 and its downstream intron have not previously been described, but they are shown herein to be effective at facilitating exon skipping. For instance, these AONs can include 5'-UCACCACU-3' (SEQ ID NO: 22), 5'-ACCACUGG-3' (SEQ ID NO: 23), and/or 5'-ACUCACCA-3' (SEQ ID NO: 24).

In a third aspect, the oligonucleotide does not hybridize to the intron which is upstream of exon 80. For example, the oligonucleotide may be complementary to (part of) exon 80 but not to its upstream intron i.e. hybridization would occur only within the downstream intron. Similarly, the oligonucleotide can comprise a region of complementarity with (part of) exon 80, but the complementarity does not extend into the upstream intron (and, in some embodiments, it does not even extend into either intron which flanks exon 80). Thus, when aligned with exon 80 according to base-pairing (e.g. as shown in FIG. 1) the oligonucleotide will not include any base-pairs with the upstream intron (and, in some embodiments, with neither the upstream nor the downstream intron). In contrast, AONs of the prior art span exon 80 and its upstream intron (see the 'ESE' oligonucleotides in FIG. 1).

In a fourth aspect, the oligonucleotide comprises a region of complementarity with exon 80 that is at most 20 nucleotides in length (e.g. at most 11, 12, 13, 14, 15, 16, 17, 18, 19, or 20 nucleotides; such as at most 11-17). In contrast, the known AONs of the art include a 22mer sequence within the exon. Oligonucleotides with 11-14 nucleotides complementary with exon 80 are shown herein to be very effective.

Thus an antisense oligonucleotide of the invention can comprise a (a) region of complementarity with exon 80 that is at most 20 nucleotides in length, such as 11-17 nucleotides in length, and (b) a region that is complementary to the RNA transcript in an intron upstream or downstream of exon 80 (preferably in the downstream intron).

AONs of the invention are advantageously no more than 24 nucleotides long e.g. between 20-23 nucleotides long. AONs of the invention are preferably RNA AONs. Compared with natural nucleic acids they may have chemically modified internucleosidic linkages (e.g. phosphorothioate-linkages) and they may have modified sugars (e.g. with 2'-O-alkyl substitutions).

AONs of the invention can be formulated into pharmaceutical compositions for use in human therapy, and can be used in methods for preventing or reducing exon 80 inclusion into a mammalian, preferably human COL7A1 mRNA.

DESCRIPTION OF THE FIGURES

FIG. 1 shows a fragment (SEQ ID NO: 1) of the human COL7A1 gene including exon 80 (upper case in bold; SEQ ID NO: 18) with its 5' and 3' flanking intron boundaries (lower case; SEQ ID NO: 19 upstream, and SEQ ID NO: 20 downstream), depicting underneath the various antisense oligonucleotides (AONs) tested herein (shown in 3' to 5' orientation). ESE80.3 and ESE80.3_Q2I70X were disclosed in WO2013/053819; the other AONs are those according to the invention. The underlined nucleotides in the RNA transcript exon 80 represent the most frequent exon 80 mutations found in EB patients. Use of lower and upper case is only to facilitate recognition of exon (upper case) and intron (lower case) sequences and boundaries, and for ease of alignment of oligonucleotides with their complementary target sequence. SEQ ID NO: 22, 23 and 24 are sequences within or partly overlapping with the different AONs of the present invention.

FIG. 7 shows cell viability of RAW-blue macrophages after the indicated treatments, including three doses for each of AON80.5 and AON80.5.1. The y-axis shows resorufin levels ($\lambda_{Ex560nm}/\lambda_{Em590nm}$), indicating the fold-change relative to saline. **$P<0.0001$, $P<0.01$, *$P<0.05$.

DETAILED DESCRIPTION OF THE INVENTION

Figure 2:
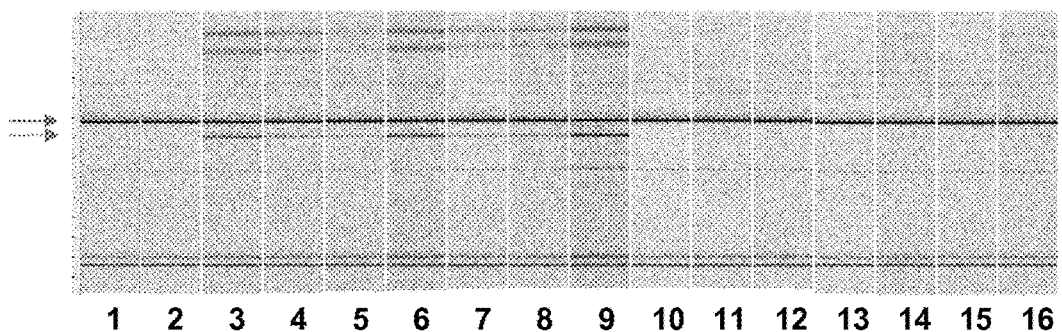
FIG. 2 shows lab-on-a-chip results for exon skipping on human primary fibroblasts (HPF) treated with the AONs described herein. The full-length band and the exon 80 skipped band are indicated with arrows. Lanes 1-16 are, from left to right: empty control; maxPei control; ESE80.3; ESE80.3_Q2I70X; AON80.1; AON80.2; AON80.3; AON80.4; AON80.5; AON80.6; AON80.7; AON80.8; AON80.9; AON80.10; AON80.11; and AON80.12. Upper arrow indicates full length mRNA product, the lower arrow indicates mRNA product with exon 80 excluded.
Figure 3:
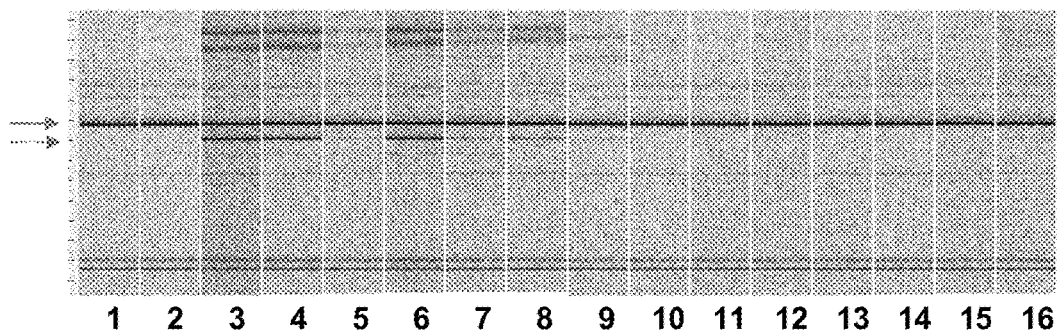
FIG. 3 shows lab-on-a-chip results for exon skipping on HeLa cells treated with AONs. The location of the full-length band and the exon 80 skipped band are the same as in FIG. 2, as are lanes 1-16.
Figure 4:
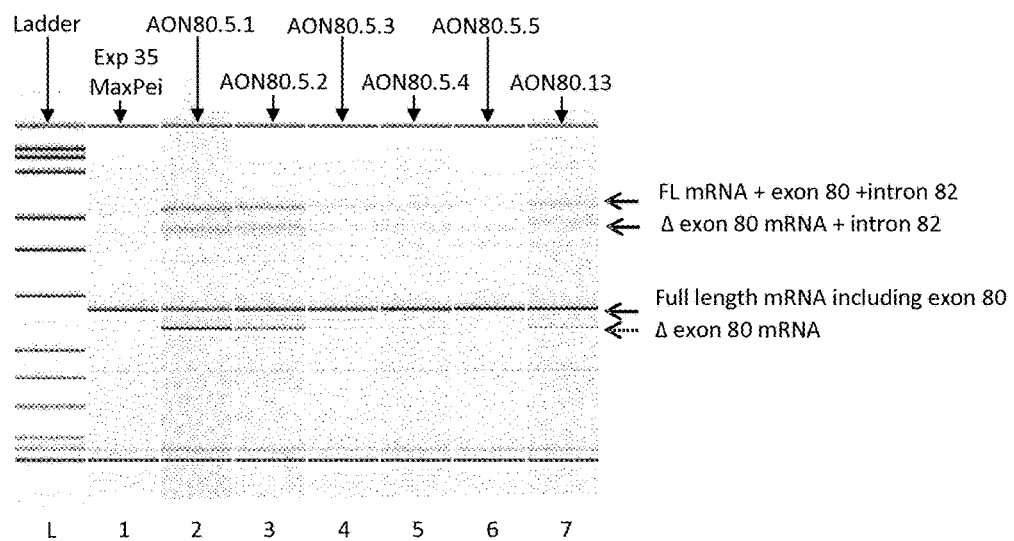
FIG. 4 shows lab-on-a-chip results of AONs, optimized from AON80.5 and tested on HPFs. AON80.5.1, AON80.5.2 and AON80.13 have higher splicing efficiency than AON80.5.3, AON80.5.4 and AON80.5.5. To assess the exact sequence of all the product formed, sequence analysis was performed. Extra products visible after analysis with the bioanalyzer (upper two arrows) are those that have intron 82 included in the mRNA (as detected with sequencing analysis). Presence of intron 82 results in the presence of a stop codon, which will likely lead to degradation of the protein. FL=full length.
Figure 5:
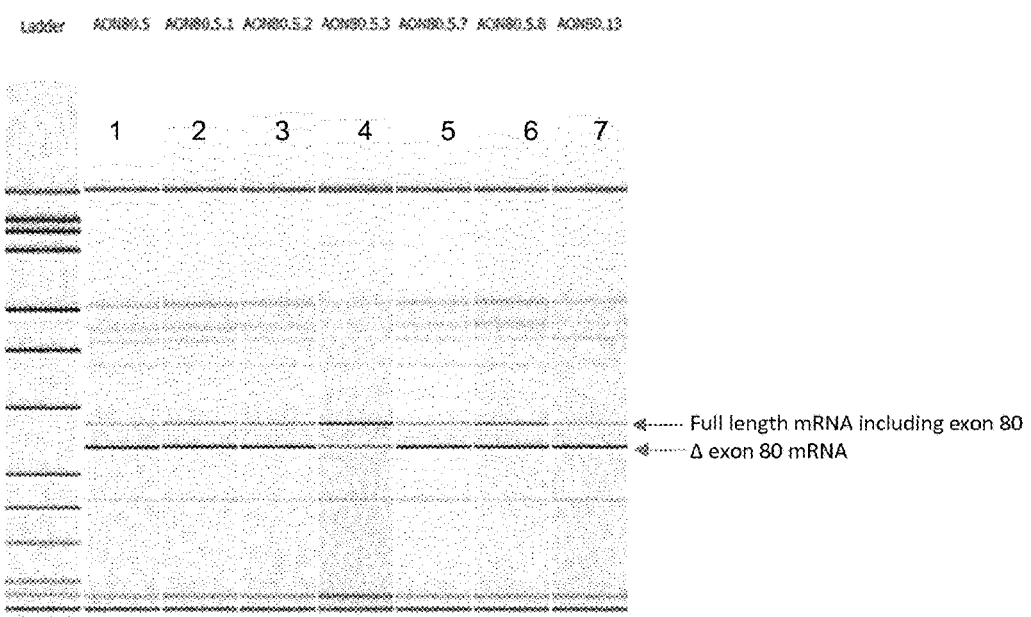
FIG. 5 shows lab-on-a-chip results for exon skipping on HPFs treated with the optimized AONs compared to AON80.5. The upper arrow indicates full-length mRNA and the lower arrow indicates mRNA wherein exon 80 is excluded. Lanes 1-7 are: AON80.5, AON80.5.1, AON80.5.2, AON80.5.3, AON80.5.7, AON80.5.8 and AON80.13.

Surprisingly, antisense oligonucleotides (AONs) have been obtained that have similar or better exon skipping characteristics in the assays disclosed herein compared to those disclosed in the prior art. These AONs of the present invention can be used as active drug substances in therapies to treat human disease, more in particular epidermolysis bullosa (EB), still more in particular EB associated with mutations in COL7A1 exon 80. These AONs may be used as sole active drug substance, in combination with other AONs targeting COL7A1 exon 80 (including those disclosed herein) and/or in combination with other active drug substances for treating EB disease. Such other drug substances may be other AONs, for example those targeting mutations in other exons (including exons 73, 74 or 3), or non-AON active drug substances. Combination therapy may be in the form of a single composition or multiple compositions, administered simultaneously or consecutively.

The present invention relates to an AON capable of preventing or reducing exon 80 inclusion into a human COL7A1 mRNA when said mRNA is produced by splicing from a pre-mRNA in a cell, characterized in that the AON comprises a nucleotide sequence: that is complementary to at least a part of exon 80 and that is not complementary to the upstream intron of exon 80 of the COL7A1 gene; or that is complementary to at least a part of exon 80 and is less than 24 nucleotides in length. In a preferred embodiment, the AON according to the invention comprises a region of complementarity with exon 80 wherein said region of complementarity is at most 20 nucleotides in length, preferably 11, 12, 13, 14, 15, 16 or 17 nucleotides. More preferably, said AON comprises a nucleotide sequence that is complementary to a 3' part of exon 80 and a 5' part of the downstream intron. Even more preferably, the AON comprises the nucleotide sequence 5'-UCACCACU-3' (SEQ ID NO: 22), 5'-ACCACUGG-3' (SEQ ID NO: 23), or 5'-ACUCACCA-3' (SEQ ID NO: 24). Most preferably, the AON according to the invention comprises a nucleotide sequence selected from the group consisting of: SEQ ID NO: 7, 8, 25, 26, 28, 31 and 32.

In another embodiment, the invention relates to an AON according to the invention that is less than 24 nucleotides in length, preferably comprising 20, 21, 22, or 23 nucleotides. Preferably, said AON comprises a nucleotide sequence of SEQ ID NO: 4 or 5, more preferably said AON comprises the nucleotide sequence of SEQ ID NO: 6, or wherein the AON comprises the nucleotide sequence of SEQ ID NO: 30.

The AONs according to the invention—apart from their effectiveness—have certain advantages over those disclosed in the prior art in terms of manufacturability, analytics and/or cost of goods, in the sense that the AONs of the invention are preferably shorter than those disclosed in the prior art.

Preferred AONs of the invention are less than 24, such as 20, 21, 22 or 23 nucleotides in length. Where an AON is complementary only to exon 80 and not to either of its flanking introns (as shown herein), it can be any length up to the 36 nt length of the whole exon (e.g. AON80.13).

The shortened mRNA, lacking the entire exon 80 as a result of treatment using AONs of the invention, will be translated into a shorter but functional COL VII protein. In some instances, however, the use of certain AONs of the present invention do also lead to longer transcripts being formed (e.g. sequences from intron 82), which may lead to expression of a (non-functional and easily degradable) protein alongside the shorter (functional) protein.

Surprisingly, AONs have been identified which are capable of preventing or reducing exon 80 inclusion into a human COL7A1 mRNA, when said mRNA is produced by splicing from a pre-mRNA in a mammalian cell, characterized in that said oligonucleotide's sequence is complementary to a 3' part of exon 80 and a 5' part of the downstream intron (for instance (partly) complementary to the 24mer 5'-CCTGGCCCAGTGgtgagtacccaa-3' (SEQ ID NO: 21) that has 12 exon nucleotides and 12 intron nucleotides). Previously, no AONs have been described that cover the boundary between exon 80 and its downstream intron. Such AONs may comprise, for example: (i) the sequence 5'-UCACCACU-3' (SEQ ID NO: 22), thus including at least 4 nucleotides from either side of the exon/intron boundary; (ii) the sequence 5'-ACCACUGG-3' (SEQ ID NO: 23), thus including at least 2 nucleotides from the intron side of the boundary and at least 6 nucleotides from the exon side; and/or (iii) the sequence 5'-ACUCACCA-3' (SEQ ID NO: 24), thus including at least 6 nucleotides from the intron side of the boundary and at least 2 nucleotides from the exon side. AON80.4, AON80.5, AON80.5.1, AON80.5.2, AON80.5.3, AON80.5.4, AON80.5.5, AON80.5.7 and AON80.5.8, (see below) are examples of such AONs. An AON of this type ideally includes at least 2 nucleotides from each side of the boundary (e.g. at least 4 or 6 nucleotides from each side), but it does not need to comprise the same number of nucleotides from each side (e.g. it may have an odd number of nucleotides, such as the AON80.5 series).

Stated differently, AONs are described for the first time that are complementary to a 3' portion of exon 80, including the 3' splice site thereof, and a 5' portion of the downstream intron, and capable of preventing or reducing exon 80 inclusion into a human COL7A1 mRNA when said mRNA is produced by splicing from a pre-mRNA in a mammalian cell. These AONs, while being useful as such, are considered good candidates to be combined with other AONs capable of preventing or reducing exon 80 inclusion into a human COL7A1 mRNA, when said mRNA is produced by splicing from a pre-mRNA in a mammalian cell, especially with those AONs that are complementary to a different portion of exon 80, such as an internal portion of exon 80, or a 5' portion of exon 80 and/or the 5' boundary of exon 80 and its upstream intron. Such combinations are considered to be advantageous should it be necessary to increase the efficiency with which exon 80 is being skipped.

In other embodiments, however, an AON of the invention may hybridize only to exon 80, thus including no region which hybridizes to the introns which are upstream and downstream of exon 80. AON80.3 is an example of such an AON, as is AON80.13 (see below).

In further embodiments, an AON may hybridize to exon 80, but not to its upstream intron. AON80.3, AON80.4, AON80.5, AON80.5.1, AON80.5.2, AON80.5.3, AON80.5.4, AON80.5.5, AON80.5.7, AON80.5.8 and AON80.13 are examples of such AONs (wherein AON80.4, AON80.5, AON80.5.1, AON80.5.2, AON80.5.3, AON80.5.4, AON80.5.5, AON80.5.7 and AON80.5.8 are examples of AONs that hybridize also to the intron that is directly downstream of exon 80).

In further embodiments, an AON comprises a region of complementarity with exon 80 that is at most 20 nucleotides in length (whereas the exon-complementary regions of prior art AONs are 22 nucleotides long). Each of AON80.1, AON80.2, AON80.3, AON80.4, and AON80.5 (see Table 1 below) are examples of such AONs, having stretches of 10, 17, 20, 12, and 12 exon-complementary nucleotides, respectively. The AON80.5.1, AON80.5.2, AON80.5.3, AON80.5.4, AON80.5.5, AON80.5.7 and AON80.5.8 series are further examples (with exon overlaps of 9 to 14 nucleotides). Thus the region of complementarity with exon 80 may be between 8 and 20 (e.g. between 10 and 20 nucleotides) long, such as between 11 and 17 nucleotides, such as 11, 12, 13, 14, 15, 16 or 17 nucleotides.

For such AONs, in addition to the exon-complementary region which is <20 nucleotides long, there may be a region that is complementary to the intron upstream or downstream of exon 80. Such AONs thus include a single, essentially uninterrupted, stretch of complementarity with the nascent RNA transcript, which spans the boundary between exon 80 and one of its neighbouring introns.

Specific preferred AONs of the invention are AON80.1, AON80.2, AON80.3, AON80.4, and AON80.5 as disclosed in Table 1 and 2 below. Further preferred AONs of the invention are AON80.5.1, AON80.5.2, AON80.5.4, AON80.5.7, AON80.5.8 and AON80.13 as disclosed in Table 1 and 2. Highly preferred AONs according to the present invention are AON80.2 (SEQ ID NO: 5), AON80.5 (SEQ ID NO: 8), AON80.5.1 (SEQ ID NO: 25), AON80.5.2 (SEQ ID NO: 26), AON80.5.7 (SEQ ID NO: 31), AON80.5.8 (SEQ ID NO: 32) and AON80.13 (SEQ ID NO: 30). In another preferred embodiment, all ribose moieties are 2'-O-methylated and substantially all internucleosidic linkages are phosphorothioates.

In all embodiments of the present invention, the terms "preventing, or at least reducing, exon inclusion" and "exon skipping" are synonymous. In respect of COL7A1, "preventing, or at least reducing, exon inclusion" or "exon skipping" are to be construed as the exclusion of exon 80 (SEQ ID NO: 18, or allelic forms thereof) from the human COL7A1 mRNA (see FIG. 1). The term exon skipping is herein defined as the induction within a cell of a mature mRNA that does not contain a particular exon that would be present in the mature mRNA without exon skipping. Exon skipping is achieved by providing a cell expressing the pre-mRNA of said mature mRNA with a molecule capable of interfering with sequences such as, for example, the splice donor or splice acceptor sequence required for allowing the biochemical process of splicing, or with a molecule that is capable of interfering with an exon inclusion signal required for recognition of a stretch of nucleotides as an exon to be included in the mature mRNA; such molecules are herein referred to as exon skipping molecules.

The term pre-mRNA refers to a non-processed or partly-processed precursor mRNA that is synthesized from a DNA template in a cell by transcription.

The term "antisense oligonucleotide" is understood to refer to a nucleotide sequence which is complementary to a target nucleotide sequence in a pre-mRNA molecule, hnRNA (heterogeneous nuclear RNA) or mRNA molecule, so that it is capable of annealing with its corresponding target sequence.

The term "complementary" as used herein includes "fully complementary" and "substantially complementary", meaning there will usually be a degree of complementarity between the oligonucleotide and its corresponding target sequence of more than 80%, preferably more than 85%, still more preferably more than 90%, most preferably more than 95%. For example, for an oligonucleotide of 20 nucleotides in length with one mismatch between its sequence and its target sequence, the degree of complementarity is 95%.

The degree of complementarity of the antisense sequence is preferably such that a molecule comprising the antisense sequence can anneal to the target nucleotide sequence in the RNA molecule under physiological conditions, thereby facilitating exon skipping. It is well known to a person having ordinary skill in the art, that certain mismatches are more permissible than others, because certain mismatches have less effect on the strength of binding, as expressed in terms of melting temperature or Tm, between AON and target sequence, than others. Certain non-complementary basepairs may form so-called "wobbles" that disrupt the overall binding to a lesser extent than true mismatches. The length of the AON also plays a role in the strength of binding, longer AONs having higher melting temperatures as a rule than shorter AONs, and the G/C content of an oligonucleotide is also a factor that determines the strength of binding, the higher the G/C content the higher the melting temperature for any given length. Certain chemical modifications of the nucleobases or the sugar-phosphate backbone, as contemplated by the present invention, may also influence the strength of binding, such that the degree of complementarity is only one factor to be taken into account when designing an oligonucleotide according to the invention.

The presence of a CpG or multitude (two or more) of CpGs in an oligonucleotide is usually associated with an increased immunogenicity of said oligonucleotide (Dorn and Kippenberger, 2008). This increased immunogenicity is undesired since it may induce damage of the tissue to be treated, i.e. the skin (dermis and/or epidermis). Thus it is preferred that an AON of the invention includes no more than 1 or 2 CpG dinucleotide sequences (preferably only one).

The invention allows designing an oligonucleotide with acceptable RNA binding kinetics and/or thermodynamic properties. The RNA binding kinetics and/or thermodynamic properties are at least in part determined by the melting temperature of an oligonucleotide (Tm; calculated with the oligonucleotide properties calculator (www.unc.edu/~cail/biotool/oligo/index.html) for single stranded RNA using the basic Tm and the nearest neighbor models), and/or the free energy of the AON-target exon complex (using RNA structure version 4.5). If a Tm is too high, the oligonucleotide is expected to be less specific. An acceptable Tm and free energy depend on the sequence of the oligonucleotide, the chemistry of the backbone (phosphodiester, phosphorothioate, phosphoramidate, peptide-nucleic acid, etc.), the nature of the sugar moiety (ribose, deoxyribose, substituted ribose, intramolecular bridge) and chemical modification of the nucleobase. Therefore, the range of Tm can vary widely.

The exon skipping percentage or efficiency may be calculated by determining the concentration of wild-type band amplified, divided by the concentration of the shortened (exon 80-free) band amplified, after a given number of PCR cycles, times 100%, for any given primer set, provided the number of cycles is such that the amplification is still in the exponential phase. Quantification can be performed using the Agilent 2100 Bioanalyzer in combination with DNA1000 kit.

Preferably, an AON according to the invention, which comprises a sequence that is complementary to a nucleotide sequence as shown in SEQ ID NO: 1 is such that the complementary part is at least about 80%, more preferably at least about 90%, still more preferably at least about 95%, most preferably about 100% complementary to the target sequence. It is thus not absolutely required that all the bases in the region of complementarity are capable of pairing with bases in the opposing strand. For instance, when designing the oligonucleotide one may want to incorporate for instance a residue that does not base pair with the base on the complementary strand. Mismatches may, to some extent, be allowed, if under the circumstances in the cell, the stretch of nucleotides is sufficiently capable of hybridizing to the complementary part. In this context, "sufficiently" means that the AONs according to the invention are capable of inducing exon skipping of exon 80. Skipping the targeted exon may conveniently be assessed by PCR/Bioanalyzer, optionally ddPCR. The complementary regions are preferably designed such that, when combined, they are specific for the exon in the pre-mRNA. Such specificity may be created with various lengths of complementary regions as this depends on the actual sequences in other (pre-)mRNA molecules in the system. The risk that the oligonucleotide also will be able to hybridize to one or more other pre-mRNA molecules decreases with increasing size of the oligonucleotide, while the length should not be too long to create problems with manufacturability, purification and/or analytics.

It is clear that oligonucleotides comprising mismatches in the region of complementarity but that retain the capacity to hybridize and/or bind to the targeted region(s) in the pre-mRNA, can be used in the present invention. However, preferably at least the complementary parts do not comprise such mismatches as these typically have a higher efficiency and a higher specificity, than oligonucleotides having such mismatches in one or more complementary regions. It is thought, that higher hybridization strengths, (i.e. increasing number of interactions with the opposing strand) are favorable in increasing the efficiency of the process of interfering with the splicing machinery of the system. Preferably, the complementarity is from 90% to 100%. In general this allows for 1 or 2 mismatch(es) in an oligonucleotide of 20 nucleotides.

An exon skipping molecule of the invention is preferably an (antisense) oligonucleotide, which is complementary to an exon 80 sequence (SEQ ID NO: 18) within SEQ ID NO: 1.

Preferably, the length of the complementary part of the oligonucleotide is the same as the length of the oligonucleotide, meaning there are no 5' or 3' ends of the oligo that do not form a basepair with the target RNA. Thus a preferred length for an oligonucleotide of the invention is 23 nucleotides or less e.g. 11, 12, 13, 14, 15, 16, 17, 18, 19, 20, 21, 22 or 23.

Particularly good results have been obtained with AONs having a length of 20, 21 or 23 nucleotides.

Where an AON is complementary only to exon 80 and not to either of its flanking introns, it may be any length e.g. from 12-36 nucleotides long e.g. a 20mer (e.g. AON80.3) or a 36mer (e.g. AON80.13).

An exon skipping molecule according to the invention may contain one of more DNA residues (consequently a RNA "u" residue will be a "t" residue as DNA counterpart), or one or more RNA residues, and/or one or more nucleotide analogues or equivalents, as will be further detailed herein below. SEQ ID NOs: 4-15 and 25-32 are RNA sequences, but the invention also encompasses each of these sequences in DNA form, and also chimeric DNA/RNA AONs of these sequences.

It is preferred that an exon skipping molecule of the invention comprises one or more residues that are modified to increase nuclease resistance, and/or to increase the affinity of the antisense oligonucleotide for the target sequence. Therefore, in a preferred embodiment, the antisense nucleotide sequence comprises at least one nucleotide analogue or equivalent, wherein a nucleotide analogue or equivalent is defined as a residue having a modified base, and/or a modified backbone, and/or a non-natural internucleoside linkage, or a combination of these modifications.

In a preferred embodiment, the nucleotide analogue or equivalent comprises a modified backbone. Examples of such backbones are provided by morpholino backbones, carbamate backbones, siloxane backbones, sulfide, sulfoxide and sulfone backbones, formacetyl and thioformacetyl backbones, methyleneformacetyl backbones, riboacetyl backbones, alkene containing backbones, sulfamate, sulfonate and sulfonamide backbones, methyleneimino and methylenehydrazino backbones, and amide backbones. Phosphorodiamidate morpholino oligomers are modified backbone oligonucleotides that have previously been investigated as antisense agents. Morpholino oligonucleotides have an uncharged backbone in which the deoxyribose sugar of DNA is replaced by a six membered ring and the phosphodiester linkage is replaced by a phosphorodiamidate linkage. Morpholino oligonucleotides are resistant to enzymatic degradation and appear to function as antisense agents by arresting translation or interfering with pre-mRNA splicing rather than by activating RNase H. Morpholino oligonucleotides have been successfully delivered to tissue culture cells by methods that physically disrupt the cell membrane, and one study comparing several of these methods found that scrape loading was the most efficient method of delivery; however, because the morpholino backbone is uncharged, cationic lipids are not effective mediators of morpholino oligonucleotide uptake in cells.

According to one embodiment of the invention the linkage between the residues in a backbone do not include a phosphorus atom, such as a linkage that is formed by short chain alkyl or cycloalkyl internucleoside linkages, mixed heteroatom and alkyl or cycloalkyl internucleoside linkages, or one or more short chain heteroatomic or heterocyclic internucleoside linkages.

In accordance with this embodiment, a preferred nucleotide analogue or equivalent comprises a Peptide Nucleic Acid (PNA), having a modified polyamide backbone (Nielsen et al. 1991). PNA-based molecules are true mimics of DNA molecules in terms of base-pair recognition. The backbone of the PNA is composed of N-(2-aminoethyl)-glycine units linked by peptide bonds, wherein the nucleobases are linked to the backbone by methylene carbonyl bonds. An alternative backbone comprises a one-carbon extended pyrrolidine PNA monomer (Govindaraju and Kumar. 2005). Since the backbone of a PNA molecule contains no charged phosphate groups, PNA-RNA hybrids are usually more stable than RNA-RNA or RNA-DNA hybrids, respectively (Egholm et al. 1993).

According to another embodiment of the invention, the backbone comprises a morpholino nucleotide analog or equivalent, in which the ribose or deoxyribose sugar is replaced by a 6-membered morpholino ring. A most preferred nucleotide analog or equivalent comprises a phosphorodiamidate morpholino oligomer (PMO), in which the ribose or deoxyribose sugar is replaced by a 6-membered morpholino ring, and the anionic phosphodiester linkage between adjacent morpholino rings is replaced by a non-ionic phosphorodiamidate linkage.

In yet a further embodiment, a nucleotide analogue or equivalent of the invention comprises a substitution of one of the non-bridging oxygens in the phosphodiester linkage. This modification slightly destabilizes base-pairing but adds significant resistance to nuclease degradation. A preferred nucleotide analogue or equivalent comprises phosphorothioate, chiral phosphorothioate, phosphorodithioate, phosphotriester, aminoalkylphosphotriester, H-phosphonate, methyl and other alkyl phosphonate including 3'-alkylene phosphonate, 5'-alkylene phosphonate and chiral phosphonate, phosphinate, phosphoramidate including 3'-amino phosphoramidate and aminoalkylphosphoramidate, thionophosphoramidate, thionoalkylphosphonate, thionoalkylphosphotriester, selenophosphate or boranophosphate.

A further preferred nucleotide analogue or equivalent of the invention comprises one or more sugar moieties that are mono- or disubstituted at the 2', 3' and/or 5' position such as a —OH; —F; substituted or unsubstituted, linear or branched lower (C1-C10) alkyl, alkenyl, alkynyl, alkaryl, allyl, or aralkyl, that may be interrupted by one or more heteroatoms; O-, S-, or N-alkyl; O-, S-, or N-alkenyl; O-, S- or N-alkynyl; O-, S-, or N-allyl; O-alkyl-O-alkyl, -methoxy, -aminopropoxy; methoxyethoxy; -dimethylaminooxyethoxy; and -dimethylaminoethoxyethoxy. The sugar moiety can be a furanose or derivative thereof, or a deoxyfuranose or derivative thereof, preferably ribose or derivative thereof, or deoxyribose or derivative of. A preferred derivatized sugar moiety comprises a Locked Nucleic Acid (LNA), in which the 2'-carbon atom is linked to the 3' or 4' carbon atom of the sugar ring thereby forming a bicyclic sugar moiety. A preferred LNA comprises 2'-0,4'-C-ethylene-bridged nucleic acid (Morita et al. 2001. Nucleic Acid Res Supplement No. 1: 241-242). These substitutions render the nucleotide analogue or equivalent RNase H and nuclease resistant and increase the affinity for the target RNA.

It is understood by a skilled person that it is not necessary for all internucleosidic linkages in an antisense oligonucleotide to be modified. For example, some internucleosidic linkages may be unmodified, whereas other internucleosidic linkages are modified. AONs comprising a backbone consisting of one form of (modified) internucleosidic linkages, multiple forms of (modified) internucleosidic linkages, uniformly or non-uniformly distributed along the length of the AON are all encompassed by the present invention. In addition, any modality of backbone modification (uniform, non-uniform, mono-form or pluriform and all permutations thereof) may be combined with any form or of sugar or nucleoside modifications or analogues mentioned below.

An especially preferred backbone for the AONs according to the invention is a uniform (all) phosphorothioate (PS) backbone.

In another embodiment, a nucleotide analogue or equivalent of the invention comprises one or more base modifications or substitutions. Modified bases comprise synthetic and natural bases such as inosine, xanthine, hypoxanthine and other -aza, deaza, -hydroxy, -halo, -thio, thiol, -alkyl, -alkenyl, -alkynyl, thioalkyl derivatives of pyrimidine and purine bases that are or will be known in the art.

It is understood by a skilled person that it is not necessary for all positions in an antisense oligonucleotide to be modified uniformly. In addition, more than one of the aforementioned analogues or equivalents may be incorporated in a single antisense oligonucleotide or even at a single position within an antisense oligonucleotide. In certain embodiments, an antisense oligonucleotide of the invention has at least two different types of analogues or equivalents.

According to another embodiment AONs according to the invention comprise a 2'-O (preferably lower) alkyl phosphorothioate antisense oligonucleotide, such as 2'-O-methyl modified ribose (RNA), 2'-O-methoxyethyl modified ribose, 2'-O-ethyl modified ribose, 2'-O-propyl modified ribose, and/or substituted derivatives of these modifications such as halogenated derivatives.

An effective and preferred antisense oligonucleotide format according to the invention comprises 2'-O-methyl modified ribose moieties with a phosphorothioate backbone, preferably wherein substantially all ribose moieties are 2'-O-methyl and substantially all internucleosidic linkages are phosphorothioate linkages.

It will also be understood by a skilled person that different AONs can be combined for efficiently skipping of exon 80 of the COL7A1 gene. A combination of two AONs may be used in a method of the invention, such as two AONs, three different AONs, four different AONs, or five different AONs targeting the same or different regions of exon 80 (FIG. 1), as long as at least one AON is one according to the invention.

An AON can be linked to a moiety that enhances uptake of the AON in cells, preferably skin cells. Examples of such moieties are cholesterols, carbohydrates, vitamins, biotin, lipids, phospholipids, cell-penetrating peptides including but not limited to antennapedia, TAT, transportan and positively charged amino acids such as oligoarginine, poly-arginine, oligolysine or polylysine, antigen-binding domains such as provided by an antibody, a Fab fragment of an antibody, or a single chain antigen binding domain such as a camelid single domain antigen-binding domain.

An exon skipping molecule according to the invention may be a naked (gymnotic) AON or in the form of a conjugate or expressed from a vector (vectored AON). The exon skipping molecule may be administrated using suitable means known in the art. When the exon skipping molecule is a vectored AON, it may for example be provided to an individual or a cell, tissue or organ of said individual in the form of an expression vector wherein the expression vector encodes a transcript comprising said oligonucleotide. The expression vector is preferably introduced into a cell, tissue, organ or individual via a gene delivery vehicle, such as a viral vector. In a preferred embodiment, there is provided a viral-based expression vector comprising an expression cassette or a transcription cassette that drives expression or transcription of an exon skipping molecule as identified herein. Accordingly, the present invention provides a viral vector expressing an exon skipping molecule according to the invention when placed under conditions conducive to expression of the exon skipping molecule. A cell can be provided with an exon skipping molecule capable of interfering with sequences essential for, or at least conducive to, exon 80 inclusion, such that such interference prevents, or at least reduces, exon 80 inclusion into the COL7A1 mRNA, for example by plasmid-derived AON expression or viral expression provided by adenovirus- or adeno-associated virus-based vectors. Expression may be driven by a polymerase III promoter, such as a U1, a U6, or a U7 RNA promoter. A preferred delivery vehicle is a viral vector such as an adeno-associated virus vector (AAV), or a retroviral vector such as a lentivirus vector and the like. Also, plasmids, artificial chromosomes, plasmids usable for targeted homologous recombination and integration in the mammalian (preferably human) genome of cells may be suitably applied for delivery of an oligonucleotide as defined herein. Preferred for the current invention are those vectors wherein transcription is driven from Pol-III promoters, and/or wherein transcripts are in the form of fusions with U1 or U7 transcripts, which yield good results for delivering small transcripts. It is within the skill of the artisan to design suitable transcripts. Preferred are Pol-III driven transcripts. Preferably, in the form of a fusion transcript with an U1 or U7 transcript. Such fusions may be generated as described in the art (e.g. vide: Gorman L et al., 1998 or Suter D et al., 1999).

One preferred AON expression system is an adenovirus associated virus (AAV)-based vector. Single chain and double chain AAV-based vectors have been developed that can be used for prolonged expression of AON sequences for highly efficient skipping of COL7A1 exon 80. A preferred AAV-based vector for instance comprises an expression cassette that is driven by a polymerase III-promoter (Pol III). A preferred Pol III promoter is, for example, a U1, a U6, or a U7 RNA promoter. The invention therefore also provides a viral-based vector, comprising a Pol III-promoter driven expression cassette for expression of an AON of the invention for inducing skipping of COL7A1 exon 80. An AAV vector according to the present invention is a recombinant AAV vector and refers to an AAV vector comprising part of an AAV genome comprising an encoded exon skipping molecule according to the invention encapsidated in a protein shell of capsid protein derived from an AAV serotype as depicted elsewhere herein. Part of an AAV genome may contain the inverted terminal repeats (ITR) derived from an adeno-associated virus serotype, such as AAV1, AAV2, AAV3, AAV4, AAV5, AAV8, AAV9 and others. Protein shell comprised of capsid protein may be derived from an AAV serotype such as AAV1, 2, 3, 4, 5, 8, 9 and others. A protein shell may also be named a capsid protein shell. AAV vector may have one or preferably all wild type AAV genes deleted, but may still comprise functional ITR nucleic acid sequences. Functional ITR sequences are necessary for the replication, rescue and packaging of AAV virions. The ITR sequences may be wild type sequences or may have at least 80%, 85%, 90%, 95, or 100% sequence identity with wild type sequences or may be altered by for example in insertion, mutation, deletion or substitution of nucleotides, as long as they remain functional. In this context, functionality refers to the ability to direct packaging of the genome into the capsid shell and then allow for expression in the host cell to be infected or target cell. In the context of the present invention a capsid protein shell may be of a different serotype than the AAV vector genome ITR. An AAV vector according to present the invention may thus be composed of a capsid protein shell, i.e. the icosahedral capsid, which comprises capsid proteins (VP1, VP2, and/or VP3) of one AAV serotype, e.g. AAV serotype 2, whereas the ITRs sequences contained in that AAV5 vector may be any of the AAV serotypes described above, including an AAV2 vector. An "AAV2 vector" thus comprises a capsid protein shell of AAV serotype 2, while e.g. an "AAV5 vector" comprises a capsid protein shell of AAV serotype 5, whereby either may encapsidate any AAV vector genome ITR according to the invention. Preferably, a recombinant AAV vector according to the present invention comprises a capsid protein shell of AAV serotype 2, 5, 8 or AAV serotype 9 wherein the AAV genome or ITRs present in said AAV vector are derived from AAV serotype 2, 5, 8 or AAV serotype 9; such AAV vector is referred to as an AAV2/2, AAV 2/5, AAV2/8, AAV2/9, AAV5/2, AAV5/5, AAV5/8, AAV 5/9, AAV8/2, AAV 8/5, AAV8/8, AAV8/9, AAV9/2, AAV9/5, AAV9/8, or an AAV9/9 vector, respectively. More preferably, a recombinant AAV vector according to the present invention has tropism for dermal and epidermal cells and comprises a capsid protein shell of AAV serotype 5 or 8. The AAV genome or ITRs present in said vector may be derived from the same or a different serotype, such as AAV serotype 2; such vector is referred to as an AAV 2/5 or AAV 2/8 vector. AAV with a serotype 5 capsid have tropism for dermal and epidermal cells, such as basilar and suprabasilar keratinocytes and dermal fibroblasts. AAV vectors with a type 5 capsid display much higher transduction efficiencies compared to AAV with a type 2 capsid (Keswani et al. 2012). Similarly, AAV with a capsid of serotype 8 show tropism towards dermal fibroblasts and (mainly) suprabasilar keratinocytes. Moreover, AAV 2/8 tend to be more efficient in transducing mammalian, preferably human dermal and epidermal cells than AAV 2/5. However, transduction efficiency appears to depend on the timing of administration during wound healing, AAV 2/2 showing higher transduction efficiencies than AAV 2/5 and AAV 2/8 at later time points (Keswani et al. 2012). Hence, AAV 2/2, AAV x/5 and AAV x/8 are preferred AAV to deliver AONs according to the invention and their choice may be determined taking into account the time of administration and the cell types to be targeted. These details can be readily worked out a person skilled in the art, in pre-clinical or clinical studies.

A nucleic acid molecule encoding an exon skipping molecule according to the present invention represented by a nucleic acid sequence of choice is preferably inserted between the AAV genome or ITR sequences as identified above, for example an expression construct comprising an expression regulatory element operably linked to a coding sequence and a 3' termination sequence.

"AAV helper functions" generally refers to the corresponding AAV functions required for AAV replication and packaging supplied to the AAV vector in trans. AAV helper functions complement the AAV functions which are missing in the AAV vector, but they lack AAV ITRs (which are provided by the AAV vector genome). AAV helper functions include the two major ORFS of AAV, namely the rep coding region and the cap coding region or functional substantially identical sequences thereof. Rep and Cap regions are well known in the art, see e.g. Chiorini et al. (1999) or U.S. Pat. No. 5,139,941, incorporated herein by reference. The AAV helper functions can be supplied on an AAV helper construct, which may be a plasmid. Introduction of the helper construct into the host cell can occur e.g. by transformation, transfection, or transduction prior to or concurrently with the introduction of the AAV genome present in the AAV vector as identified herein. The AAV helper constructs of the invention may thus be chosen such that they produce the desired combination of serotypes for the AAV vector's capsid protein shell on the one hand and for the AAV genome present in said AAV vector replication and packaging on the other hand.

"AAV helper virus" provides additional functions required for AAV replication and packaging. Suitable AAV helper viruses include adenoviruses, herpes simplex viruses (such as HSV types 1 and 2) and vaccinia viruses. The additional functions provided by the helper virus can also be introduced into the host cell via vectors, as described in U.S. Pat. No. 6,531,456 incorporated herein by reference. Preferably, an AAV genome as present in a recombinant AAV vector according to the present invention does not comprise any nucleotide sequences encoding viral proteins, such as the rep (replication) or cap (capsid) genes of AAV. An AAV genome may further comprise a marker or reporter gene, such as a gene for example encoding an antibiotic resistance gene, a fluorescent protein (e.g. gfp) or a gene encoding a chemically, enzymatically or otherwise detectable and/or selectable product (e.g. lacZ, aph, etc.) known in the art. A preferred AAV vector according to the present invention is an AAV vector, preferably an AAV2/5, AAV2/8, AAV2/9 or AAV2/2 vector, expressing an exon skipping molecule according to the present invention comprising an antisense oligonucleotide, wherein said antisense oligonucleotide comprises or consists of a sequence selected from the group consisting of: AON80.1, AON80.2, AON80.3, AON80.4 and AON80.5 as disclosed in Table 1 below. Improvements in means for providing an individual or a cell, tissue, organ of said individual with an exon skipping molecule according to the invention, are anticipated considering the progress that has already thus far been achieved. Such future improvements may of course be incorporated to achieve the mentioned effect on restructuring of mRNA using a method of the invention. An exon skipping molecule according to the invention can be delivered as is to an individual, a cell, tissue or organ of said individual. When administering an exon skipping molecule according to the invention, it is preferred that the molecule is dissolved in a solution that is compatible with the delivery method.

Gymnotic AONs are readily taken up by most cells in vivo, and usually dissolving the AONs according to the invention in an isotonic (saline) solution will be sufficient to reach the target cells, such as skin (dermis and epidermis) cells. Alternatively, gymnotic AONs of the invention may be formulated using pharmaceutically acceptable excipients, additives, stabilizers, solvents, colorants and the like. In addition, or alternatively, gymnotic AONs may be formulated with any of the transfection aids mentioned below.

Skin (dermis and epidermis) cells can be provided with a plasmid for antisense oligonucleotide expression by providing the plasmid in an aqueous solution, such as an isotonic (saline) solution. Alternatively, a plasmid can be provided by transfection using known transfection agents.

For intravenous, subcutaneous, intramuscular, intrathecal and/or intraventricular administration it is preferred that the solution is an isotonic (saline) solution. Particularly preferred in the invention is the use of an excipient or transfection agents that will aid in delivery of each of the constituents as defined herein to a cell and/or into a cell, preferably a skin (dermis and epidermis) cell. Preferred are excipients or transfection agents capable of forming complexes, nanoparticles, micelles, vesicles and/or liposomes that deliver each constituent as defined herein, complexed or trapped in a vesicle or liposome through a cell membrane. Many of these excipients are known in the art. Suitable excipients or transfection agents comprise polyethylenimine (PEI; ExGen500 (MBI Fermentas)), LipofectAMINE™ 2000 (Invitrogen) or derivatives thereof, or similar cationic polymers, including polypropyleneimine or polyethylenimine copolymers (PECs) and derivatives, synthetic amphiphils (SAINT-18), Lipofectin™, DOTAP and/or viral capsid proteins that are capable of self-assembly into particles that can deliver each constitutent as defined herein to a cell, preferably a skin (dermis r epidermis) cell. Such excipients have been shown to efficiently deliver an oligonucleotide such as antisense nucleic acids to a wide variety of cultured cells, including skin (dermis and epidermis) cells. Their high transfection potential is combined with an acceptably low to moderate toxicity in terms of overall cell survival. The ease of structural modification can be used to allow further modifications and the analysis of their further (in vivo) nucleic acid transfer characteristics and toxicity.

Lipofectin represents an example of a liposomal transfection agent. It consists of two lipid components, a cationic lipid N-[1-(2,3 dioleoyloxy)propyl]-N,N,N-trimethylammonium chloride (DOTMA) (cp. DOTAP which is the methylsulfate salt) and a neutral lipid dioleoylphosphatidylethanolamine (DOPE). The neutral component mediates the intracellular release. Another group of delivery systems are polymeric nanoparticles.

Polycations such like diethylaminoethylaminoethyl (DEAE)-dextran, which are well known as DNA transfection reagent can be combined with butylcyanoacrylate (PBCA) and hexylcyanoacrylate (PHCA) to formulate cationic nanoparticles that can deliver each constituent as defined herein, preferably an oligonucleotide, across cell membranes into cells.

In addition to these common nanoparticle materials, the cationic peptide protamine offers an alternative approach to formulate an oligonucleotide with colloids. This colloidal nanoparticle system can form so called proticles, which can be prepared by a simple self-assembly process to package and mediate intracellular release of an oligonucleotide. The skilled person may select and adapt any of the above or other commercially available alternative excipients and delivery systems to package and deliver an exon skipping molecule for use in the current invention to deliver it for the prevention, treatment or delay of a disease or condition associated with a mutated exon 80 in the COL7A1 gene.

An exon skipping molecule according to the invention could be covalently or non-covalently linked to a targeting ligand specifically designed to facilitate the uptake into the cell (especially a skin (dermis) cell), cytoplasm and/or its nucleus. Such ligand could comprise (i) a compound (including but not limited to peptide(-like) structures) recognizing cell, tissue or organ specific elements facilitating cellular uptake and/or (ii) a chemical compound able to facilitate the uptake in to cells and/or the intracellular release of an oligonucleotide from vesicles, e.g. endosomes or lysosomes.

Therefore, in a preferred embodiment, an exon skipping molecule according to the invention is formulated in a composition or a medicament or a composition, which is provided with at least an excipient and/or a targeting ligand for delivery and/or a delivery device thereof to a cell and/or enhancing its intracellular delivery.

It is to be understood that if a composition comprises an additional constituent such as an adjunct compound as later defined herein, each constituent of the composition may be formulated in one single combination or composition or preparation. Depending on their identity, the skilled person will know which type of formulation is the most appropriate for each constituent as defined herein. According to one embodiment, the invention provides a composition or a preparation which is in the form of a kit of parts comprising an exon skipping molecule according to the invention and a further adjunct compound as later defined herein.

If required, an exon skipping molecule according to the invention or a vector, preferably a viral vector, expressing an exon skipping molecule according to the invention can be incorporated into a pharmaceutically active mixture by adding a pharmaceutically acceptable carrier.

Accordingly, the invention also provides a composition, preferably a pharmaceutical composition, comprising an exon skipping molecule according to the invention, such as gymnotic AON or a viral vector according to the invention and a pharmaceutically acceptable excipient. Such composition may comprise a single exon skipping molecule according to the invention, but may also comprise multiple, distinct exon skipping molecules according to the invention. Such a pharmaceutical composition may comprise any pharmaceutically acceptable excipient, including a carrier, excipient, stabilizer, transfection agent, gelling agent, buffer, filler, preservative, adjuvant, solubilizer and/or diluent. Such pharmaceutically acceptable components may for instance be found in Remington, 2000. Each feature of said composition has earlier been defined herein.

If multiple distinct exon skipping molecules according to the invention are used, concentration or dose defined herein may refer to the total concentration or dose of all oligonucleotides used or the concentration or dose of each exon skipping molecule used or added. Therefore in one embodiment, there is provided a composition wherein each or the total amount of exon skipping molecules according to the invention used is dosed in an amount ranged from 0.0001 and 100 mg/kg, preferably from 0.001 and 50 mg/kg, still more preferably between 0.01 and 20 mg/kg.

A preferred exon skipping molecule according to the invention is for the treatment of DEB or, more generally, a mutated COL7A1 exon 80 related disease or condition of an individual. In all embodiments of the present invention, the term "treatment" is understood to include the prevention and/or delay of the disease or condition. An individual, which may be treated using an exon skipping molecule according to the invention may already have been diagnosed as having DEB or a COL7A1 exon 80 related disease or condition. Alternatively, an individual which may be treated using an exon skipping molecule according to the invention may not have yet been diagnosed, but may be an individual having an increased risk of developing DEB, or a COL7A1 exon 80 related disease or condition in the future given his or her genetic background. A preferred individual is a human being. In a preferred embodiment the mutated COL7A1 exon 80 related disease or condition is Dystrophic Epidermolysis Bullosa (DEB).

The present invention further provides an exon skipping molecule according to the invention, such as an AON, or a vector encoding an AON, such as a viral vector, according to the invention, or a composition comprising an AON, or a vector encoding an AON, according to the invention for use as a medicine e.g. for use in treating DEB or, more generally, a mutated COL7A1 exon 80 related disease or condition of an individual (as discussed above).

The invention further provides the use of an exon skipping molecule according to the invention, such as an AON, or a vector encoding an AON, such as a viral vector, according to the invention, or a composition comprising an AON, or a vector encoding an AON, according to the invention in the manufacture of a medicament for treating DEB or, more generally, a mutated COL7A1 exon 80 related disease or condition of an individual (as discussed above).

The invention further provides a method for treating a mammal (preferably a human) carrying in its genome a mutation in exon 80 of the COL7A1 gene causing a disease or disorder, including DEB, comprising administering to the mammal (human) an AON, a (viral) vector, or a pharmaceutical composition of the invention. These patients may suffer, or be at risk of developing DEB or a related disorder. Related disorder, disease or condition also encompasses for example skin cancer (melanoma), or other carcinomas, that may arise as a consequence of a collagen VII deficiency or abnormality in the skin, or other organs of an individual, caused by or associated with a mutation in exon 80 of the COL7A1 gene.

Further embodiments of the invention are AONs, viral vectors encoding AONs, and pharmaceutical compositions comprising AONs according to the invention for use as a medicine to treat a mammal (preferably a human) carrying in its genome a mutation in exon 80 of the COL7A1 gene.

Exon skipping molecules according to the invention may be administered to a patient systemically, locally, topically, through administration that is orally, intraocularly, intrapulmonary, intranasally, intramuscularly, subcutaneously, intradermally, rectally, by swallowing, injecting, inhalation, infusion, spraying, in the form of (aqueous) solutions, suspensions, (oil-in-water) emulsions, ointments, lozenges, pills etcetera.

One preferred method of administration of AONs according to the invention is by the appliance of AON-coated bandages capable of releasing the AONs. Especially beneficial are multilayered (Layer-by-Layer, LbL)-coated bandages such as disclosed in WO2014/150074. The international patent application filed in the name of MIT discloses prolonged and effective release of a wound-healing-promoting siRNA from an adhesive bandage, coated with a multilayered film containing said siRNA. A bandage that may suitably be used in combination with AONs according to the invention, is Tegaderm®. Suitable multilayer coatings for the delivery of siRNA that may also be used in combination with AONs according to the invention, comprises a Laponite® containing layer-by-layer architecture. Other bandages than Tegaderm® that are capable of releasing nucleic acid therapeutics, may be used. Also non-adhesive bandages may be used, as they are likely to be less painful for the patient, as long as the bandage is in close contact with the skin or the wound-site. AON-containing LBL films for delivery of AONs according to the invention in combination with bandages are described in WO2014/150074.

Dosing may be daily, weekly, monthly, quarterly, once per year, depending on the route of administration and the need of the patient.

Because of the early onset of disease, patients having or at risk of developing a disease, disorder or condition caused by or associated with a mutated exon 80 of the COL7A1 gene, including DEB, may be treated in utero, directly after birth, from 1, 2, 3, 6 months of age, from one year of age, from 3 years of age, from 5 years of age, prior to or after the onset of symptoms, to alleviate, retard development, stop or reverse the symptoms of disease and the like.

A treatment in a use or in a method according to the invention is at least one week, at least one month, at least several months, at least one year, at least 2, 3, 4, 5, 6 years or chronically, even during a patient's entire life. Each exon skipping molecule or exon skipping oligonucleotide or equivalent thereof as defined herein for use according to the invention may be suitable for direct administration to a cell, tissue and/or an organ in vivo of individuals already affected or at risk of developing a mutated COL7A1 exon 80 related disorder, disease or condition, and may be administered directly in vivo, ex vivo or in vitro. The frequency of administration of an AON, composition, compound or adjunct compound of the invention may depend on several parameters such as the age of the patient, the nature of the exon skipping molecule (e.g. gymnotic AON or vectored AON, such as AAV or lentiviral vector expressed AONs), the dose, the formulation of said molecule and the like.

Dose ranges of an exon skipping molecule, preferably an oligonucleotide according to the invention are preferably designed on the basis of rising dose studies in clinical trials (in vivo use) for which rigorous protocol requirements exist. An oligonucleotide as defined herein may be used at a dose range from 0.0001 to 100 mg/kg, preferably from 0.01 to 20 mg/kg. The dose and treatment regime may vary widely, depending on many factors, including but not limited to the route of administration (e.g. systemic versus topically), whether the oligo is administered as a gymnotic AON or as vectored AON, the dosing regimen, the age and weight of the patient, and so forth.

In a preferred embodiment, a viral vector, preferably an AAV vector as described earlier herein, as delivery vehicle for a molecule according to the invention, is administered in a dose ranging from $1\times10^9$-$1\times10^{17}$ virus particles per injection, more preferably from $1\times10^{10}$-$1\times10^{14}$, and most preferably $1\times10^{10}$-$1\times10^{12}$ virus particles per injection.

It will be clear to a person having ordinary skill in the art to which this invention pertains, that the details of treatment will need to be established in accordance with and depending on such factors as the sequence and chemistry of the oligonucleotide(s), the route of administration, the formulation, the dose, the dosing regimen, the format (viral vector or gymnotic oligonucleotide), the age and weight of the patient, the stage of the disease and so forth, which may require further non-clinical and clinical investigation.

The invention further provides a method for preventing, or at least reducing, COL7A1 exon 80 inclusion in a cell comprising contacting the cell, preferably a skin (dermis) cell, with an exon skipping molecule according to the invention, such as a gymnotic AON or a (viral) vector encoding an AON according to the invention, or a composition according to the invention. The features of this aspect are preferably those defined earlier herein.

Unless otherwise indicated each embodiment as described herein may be combined with another embodiment as described herein.

The present invention relates to an antisense oligonucleotide capable of preventing or reducing exon 80 inclusion into a human COL7A1 mRNA, when said mRNA is produced by splicing from a pre-mRNA in a mammalian cell; characterized in that the oligonucleotide (a) comprises a nucleotide sequence which is complementary to part of exon 80 and (b) is less than 24 nucleotides in length.

In another aspect the invention relates to an antisense oligonucleotide capable of preventing or reducing exon 80 inclusion into a human COL7A1 mRNA, when said mRNA is produced by splicing from a pre-mRNA in a mammalian cell; characterized in that the oligonucleotide comprises a nucleotide sequence which is complementary to a 3' part of exon 80 and a 5' part of the downstream intron. Preferably, said oligonucleotide comprises a nucleotide sequence which is complementary to SEQ ID NO: 21. For example, said oligonucleotide comprises SEQ ID NO: 22 (5'-UCAC-CACU-3'), SEQ ID NO: 23 (5'-ACCACUGG-3'), and/or SEQ ID NO: 24 (5'-ACUCACCA-3').

In another aspect the invention relates to an antisense oligonucleotide capable of preventing or reducing exon 80 inclusion into a human COL7A1 mRNA, when said mRNA is produced by splicing from a pre-mRNA in a mammalian cell; characterized in that the oligonucleotide comprises SEQ ID NO: 22 (5'-UCACCACU-31 SEQ ID NO: 23 (5'-ACCACUGG-3'), and/or SEQ ID NO: 24 (5'-ACU-CACCA-3').

Preferably, an oligonucleotide according to the present invention is less than 24 nucleotides, in certain embodiments preferably between 20 and 23 nucleotides, in length. Hence, preferably, said oligonucleotide is 20, 21, 22 or 23 nucleotides in length.

In a preferred aspect, the oligonucleotide is selected from the group consisting of AON80.1, AON80.2, AON80.3, AON80.5, AON80.5.1, AON80.5.2, AON80.5.3, AON80.5.4, AON80.5.5, AON80.5.7 and AON80.5.8. Preferably, said oligonucleotide is selected from the groups consisting of:
(i) AON80.2 and AON80.5;
(ii) AON80.5.1, AON80.5.2, AON80.5.3, AON80.5.4, and AON80.5.5; or
(iii) AON80.5.1, AON80.5.2, AON80.5.3, AON80.5.4, AON80.5.5, AON80.5.7 and AON80.5.8.

In yet another preferred embodiment, the oligonucleotide is selected from the group consisting of AON80.4, AON80.5, AON80.5.1, AON80.5.2, AON80.5.3, AON80.5.4, AON80.5.5, AON80.5.7 and AON80.5.8.

The present invention also relates to an antisense oligonucleotide capable of preventing or reducing exon 80 inclusion into the human COL7A1 mRNA, when said mRNA is produced by splicing from an RNA transcript in a mammalian cell, characterized in that said antisense oligonucleotide does not hybridize to the intron which is upstream of exon 80. Preferably, said mammalian cell is a human cell. Preferably the sequence of said oligonucleotide comprises the sequence of an oligonucleotide of the group consisting of AON80.3, AON80.4, AON80.5, AON80.5.1, AON80.5.2, AON80.5.3, AON80.5.4, AON80.5.5, AON80.5.7, AON80.5.8 and AON80.13.

In another embodiment, the invention relates to an antisense oligonucleotide capable of preventing or reducing exon 80 inclusion into the human COL7A1 mRNA, when said mRNA is produced by splicing from an RNA transcript in a mammalian cell, characterized in that said antisense oligonucleotide is complementary to exon 80 but not to its upstream or downstream introns. In yet another embodiment, the invention relates to an antisense oligonucleotide capable of preventing or reducing exon 80 inclusion into a human COL7A1 mRNA, when said mRNA is produced by splicing from a pre-mRNA in a mammalian cell; wherein the oligonucleotide comprises a region of complementarity with exon 80, which region of complementarity does not extend into either of the introns which flanks exon 80. In such embodiments, the oligonucleotide is preferably AON80.3 or AON80.13.

The present invention also relates to an antisense oligonucleotide capable of preventing or reducing exon 80 inclusion into the human COL7A1 mRNA, when the mRNA is produced by splicing from an RNA transcript in a mammalian cell, characterized in that said antisense oligonucleotide comprises a region of complementarity with exon 80 that is at most 20 nucleotides in length. Preferably, said oligonucleotide comprises a sequence of an oligonucleotide from the group consisting of AON80.1, AON80.2, AON80.3, AON80.4, AON80.5, AON80.5.1, AON80.5.2, AON80.5.3, AON80.5.4, AON80.5.5, AON80.5.7 and AON80.5.8. Preferably, said region of complementarity with exon 80 is at most between 9 and 17 nucleotides, such as 9, 10, 11, 12, 13, 14, 15, 16 or 17 nucleotides. More preferably, when the oligonucleotide has a region of complementarity with the intron that is directly downstream of exon 80, the region of complementarity with exon 80 is 9 to 14 nucleotides, such as 9, 10, 11, 12, 13 or 14 nucleotides. When the portion complementary to exon 80 is at most 12 nucleotides, then the oligonucleotide is preferably selected from the group consisting of AON80.1, AON80.4, AON80.5, AON80.5.3, AON80.5.4, AON80.5.5, AON80.5.7 and AON80.5.8. In another preferred aspect, the antisense oligonucleotide comprises a (a) region of complementarity with exon 80 that is at most 20 nucleotides in length and (b) a region that is complementary to the RNA transcript in an intron upstream or downstream of exon 80. Even more preferred, the antisense oligonucleotide comprises a portion that is complementary with the RNA transcript in an intron downstream of exon 80. In one embodiment, the antisense oligonucleotide comprises a portion that is complementary to a portion of exon 80 consisting of the ten 3'-most nucleotides of SEQ ID NO: 18 (i.e. nucleotides 27-36 of SEQ ID NO: 18). In yet another embodiment, the portion of complementarity to exon 80 consists of the n-most 3' nucleotides of SEQ ID NO: 18, where n is between 9 and 20; such as 19, 18, 17, 16, 15, 14, 13, 12, 11, 10 or 9 3'-most nucleotides of SEQ ID NO: 18. In a more preferred embodiment, the portion of exon 80 consists of the 12 3'-most nucleotides of exon 80 (i.e. nucleotides 25-36 of SEQ ID NO: 18). When the oligonucleotide is complementary to part of exon 80, its sequence has preferably a length of no more than 24 nucleotides.

Regarding all antisense oligonucleotides according to the present invention, preferably the antisense oligonucleotide is an oligoribonucleotide, more preferably wherein the internucleosidic linkages are chemically modified, preferably phosphorothioate-linkages. In yet another preferred aspect, the sugar moieties of the oligonucleotide are lower 2'-O-alkyl, preferably 2'-O-methyl substituted sugar moieties.

The invention relates also to an oligonucleotide comprising or consisting of: (i) a nucleotide sequence selected from the group consisting of SEQ ID NOs: 4-17 and 25-32; (ii) a RNA nucleotide sequence selected from the group consisting of SEQ ID NOs: 4-15 and 25-32; or (iii) a DNA nucleotide sequence selected from the group consisting of SEQ ID NOs: 4-15 and 25-32 in which any U is replaced by a T.

The invention also relates to a composition comprising an oligonucleotide according to the invention, optionally comprising one or more of a carrier, excipient, stabilizer, transfection agent, diluent, gelling agent or a buffer. Preferably said composition is a pharmaceutical composition for use in human therapy, more preferably for use in the treatment of dystrophic epidermolysis bullosa (DEB), even more preferably for use in the treatment of a human subject suffering from DEB that is caused by a mutation in exon 80 of the COL7A1 gene. In another embodiment, the invention relates to an antisense oligonucleotide according to the invention for use in the treatment of a human subject that suffers from a disease caused by the inclusion of a mutated exon 80 in the COL7A1 gene.

The invention also relates to a method for preventing or reducing exon 80 inclusion into a mammalian, preferably human COL7A1 mRNA, when said mRNA is produced by splicing from a RNA transcript in a mammalian, preferably human, cell; comprising the steps of providing to a cell, to a tissue, in vitro or ex vivo, or to a living animal, including a human being, comprising such a cell, an antisense oligonucleotide according to any one of claims 1 to 27, or a composition according to claim 29 or claim 30, under conditions conducive to uptake of such oligonucleotide by such cell, and allowing splicing to take place.

The ability of an exon skipping molecule, such as an AON according to the invention, or a (viral) vector encoding such AON, to prevent, or at least reduce, mutated COL7A1 exon 80 inclusion, when the COL7A1 gene is expressed in a mammalian (preferably human) cell, and to bind to the mammalian (human) COL7A1 pre-mRNA under physiological conditions in a region affecting selection of the 5' splice acceptor, and thereby reduce inclusion of the mutated exon 80 into the COL7A1 mRNA, can be conveniently assessed using the assays disclosed in the experimental section herein. In particular, the exon skipping molecule can be incubated with a cell containing exon 80 (not necessarily mutated) of the COL7A1 gene to assess its ability to reduce production by the cell of mRNA which includes exon 80, e.g. by RT-PCR (which can be quantified using a Bioanalyzer apparatus), as described herein in the experimental section and the examples.

As can be observed in the experimental section and the Examples herein, at the RNA level, addition of various AONs according to the invention targeting exon 80 of the COL7A1 gene indeed resulted in a mRNA lacking exon 80, leading to the production of a shorter but functional collagen VII protein.

In fibroblasts (that can be derived from skin cells), collagen VII is abundantly expressed. Therefore, it is to be expected that addition of AONs to cultured fibroblasts from DEB patients will result in an increased amount of shortened but functional collagen VII protein that is detectable on Western blot, and as such will demonstrate that AON-based therapy will not only redirect splicing of the COL7A1 mRNA but will also result in restoring collagen VII functionality.

The terms "adenine", "guanine", "cytosine", "thymine", "uracil" and hypoxanthine (the nucleobase in inosine) refer to the nucleobases as such.

The terms adenosine, guanosine, cytidine, thymidine, uridine and inosine, refer to the nucleobases linked to the (deoxy)ribosyl sugar.

The term "nucleoside" refers to the nucleobase linked to the (deoxy)ribosyl sugar.

In this document and in its claims, the verb "to comprise" and its conjugations is used in its non-limiting sense to mean that items following the word are included, but items not specifically mentioned are not excluded. In addition, reference to an element by the indefinite article "a" or "an" does not exclude the possibility that more than one of the element is present, unless the context clearly requires that there be one and only one of the elements. The indefinite article "a" or "an" thus usually means "at least one".

The word "include" and all of its tenses and conjugations, is to be read as "include, but is not limited to".

The word "exon skipping molecule" is meant to include gymnotic AONs and vectored AONs, including viral vectors, capable of expressing AONs in a compatible cell.

The word "about" or "approximately" when used in association with a numerical value (e.g. about 10) preferably means that the value may be the given value (of 10) plus or minus 5% of the value.

The sequence information as provided herein should not be so narrowly construed as to require inclusion of erroneously identified bases. The skilled person is capable of identifying such erroneously identified bases and knows how to correct for such errors. In case of sequence errors, the sequence of the polypeptide obtainable by expression of the sequence present in SEQ ID NO: 1 containing the nucleic acid sequence coding for the polypeptide should prevail.

EXAMPLES

Example 1: mRNA Analysis of Exon 80

To detect the presence of mRNA of exon 80 in mRNA of COL7A1 extracted total RNA of both HeLa cells and primary human fibroblasts (HPF) cells were used. Culturing of cells was performed in (a) Dulbecco's Modified Eagle Medium (DMEM) supplemented with 10% fetal bovine serum (FBS) for HeLa, or (b) DMEM AQE supplemented with 20% FBS and 1% natrium pyruvate for HPF cells. All cells were grown at 37° C. 5% $CO_2$. To determine the exon skipping efficiency of the AONs, cells were seeded at 60.000 cells/well (HeLa) into 12-well plates or 150.000 cells/well (LFB1) into 6-well plates. After 24 hours of allowing cell growth cells were transfected with 100 nm AON-maxPei complex. RNA isolation was performed with the ReliaPrep™ RNA Cell Miniprep System (Promega). Subsequently cDNA was made using the Thermo Scientific Verso kit. PCR for exon 80 was performed with FW primer (5'-CAAGGTCCCAAAGGAGACAG-3'; SEQ ID NO: 16) located at exon 77 and a RV primer, which is either an RV primer with sequence 5'-AGTCCCACAGCTCCAGTAGG-3' (SEQ ID NO: 17) located within exon 84, or with an RV primer with sequence 5'-GAAGGGGGAGCCTGGAGA-3' (SEQ ID NO: 33) located at the exon 82/83 boundary. PCR products were visualized with the Bioanalyzer using DNA1000 chips and software Expert 2100 was used for product length analysis. Initial oligonucleotide design led to twelve oligonucleotides, AON80.1 to AON80.12, and Table 1 shows for each of these AONs the semi-quantitative skipping efficiency of exon 80 in human primary fibroblasts (HPF) and HeLa cells. Further design work based on the AON80.5 21-mer led to five derivatives, named AON80.5.1 to AON80.5.5 (all 21-mers). Also, a 36-mer oligonucleotide (AON80.13) was designed over the complete exon 80. Data for these further AONs is also included in Table 1, together with the nucleotide sequence and SEQ ID NO of preferred AONs according to the invention (AON80.1-AON80.5, and AON80.5.n series, and AON80.13). Two 20-mer oligonucleotides (AON80.5.7 and AON80.5.8) were tested in 3 experiments. Results are shown in Table 2 and show comparable results.

TABLE 1

Efficiency of exon 80 exclusion from mRNA. Cells were treated for 24 hours with 100 nM AON. For comparison ESE-80.3 and ESE-80.3_Q2170X from WO2013/053819 were used. Data are represented as: - (no exon 80 exclusion), + (1-10% exon exclusion), ++ (11-20% exon 80 exclusion), +++ (21-30% exon 80 exclusion), etc.

| AON | HPF | HeLa | Sequence 5'-3' | SEQ ID NO |
|---|---|---|---|---|
| ESE80.3 | +++ | ++++ | GGCCUCUUGGACCCUGCAGACCCU | 2 |
| ESE80.3_Q2170X | ++ | ++++ | GGCCUCUUGGACCCUACAGACCCU | 3 |
| AON80.1 | + | + | CCUGCAGACCCUACAUAGAG | 4 |
| AON80.2 | ++++ | ++++ | CUUGGACCCUGCAGACCCUA | 5 |
| AON80.3 | ++ | ++ | GGGCCUCUUGGACCCUGCAG | 6 |
| AON80.4 | ++ | +++ | UUGGGUACUCACCACUGGGCCAGG | 7 |
| AON80.5 | ++++++ | ++ | GGUACUCACCACUGGGCCAGG | 8 |
| AON80.5.1 | +++++++ | +++++++ | GUACUCACCACUGGGCCAGGG | 25 |
| AON80.5.2 | +++++ | ++++ | UACUCACCACUGGGCCAGGGG | 26 |
| AON80.5.3 | - | - | GGGUACUCACCACUGGGCCAG | 27 |
| AON80.5.4 | ++ | ++ | UGGGUACUCACCACUGGGCCA | 28 |
| AON80.5.5 | - | - | UUGGGUACUCACCACUGGGCC | 29 |
| AON80.6 | - | - | GGCAAGACAGGUGAAGGUUCUUGG | 9 |
| AON80.7 | - | - | CAGGGCACAGGAUGGGGGCAAGACA | 10 |
| AON80.8 | - | - | GUCACUGGGGCAGGGCACAGGAUGG | 11 |
| AON80.9 | - | - | CUUGGGCCUGUUCCCAACCUCUGGG | 12 |
| AON80.10 | - | - | AUCUGGGCCUCACUUGGGCCUG | 13 |
| AON80.11 | - | - | AGGGCACUGAUGAGCCUCAAUCUGG | 14 |
| AON80.12 | - | - | CAUAGAGAGGGCACUGAUGAGCCUC | 15 |
| AON80.13 | +++++++ | ++++++++ | CACUGGGCCAGGGGGGCCUCUUGGACCCUGCAGACC | 30 |

TABLE 2

Efficiency of exon 80 exclusion from mRNA. The mean results are shown for three independent experiments performed as for Table 1, with two new AONs (AON80.5.7 and AON80.5.8) and compared to AONs tested before (see above). Data are represented as in Table 1.

| AON | HPF | HeLa | Sequence 5'-3' | SEQ ID NO |
|---|---|---|---|---|
| AON80.5 | +++++++ | +++++++ | GGUACUCACCACUGGGCCAGG | 8 |
| AON80.5.1 | +++++++ | +++++++ | GUACUCACCACUGGGCCAGGG | 25 |
| AON80.5.2 | +++++ | ++++++ | UACUCACCACUGGGCCAGGGG | 26 |
| AON80.5.3 | + | - | GGGUACUCACCACUGGGCCAG | 27 |
| AON80.5.4 | ++ | ++ | UGGGUACUCACCACUGGGCCA | 28 |
| AON80.5.5 | - | - | UUGGGUACUCACCACUGGGCC | 29 |
| AON80.5.7 | ++++++ | ++++++ | GUACUCACCACUGGGCCAGG | 31 |
| AON80.5.8 | ++++++ | ++++++ | GGUACUCACCACUGGGCCAG | 32 |
| AON80.13 | +++++++ | ++++++++ | CACUGGGCCAGGGGGGCCUCUUGGACCCUGCAGACC | 30 |

FIGS. 2-5 show lab-on-a-chip results for the Table 1 and 2 AONs. The AONs according to the invention designated AON80.1 to AON80.5 have good efficiency, AON80.2, AON80.4 and AON80.5 performing better. From the further design work, AON80.5.1, AON80.5.2, AON80.5.7, AON80.5.8 and AON80.13 appear to have the best splicing efficiency of the AONs tested. Most preferred AONs according to the invention are AON80.5, AON80.5.1, AON80.5.2, AON80.5.7 and AON80.5.8.

To assess the exact sequence of all the products formed, sequence analysis was performed. Extra products visible after analysis with the bioanalyzer included intron 82 in the mRNA (as observed with sequencing analysis). If this intron would be translated to protein, however, a stop codon would be included leading to a truncated collagen protein, that most likely will be degraded.

Figure 6:
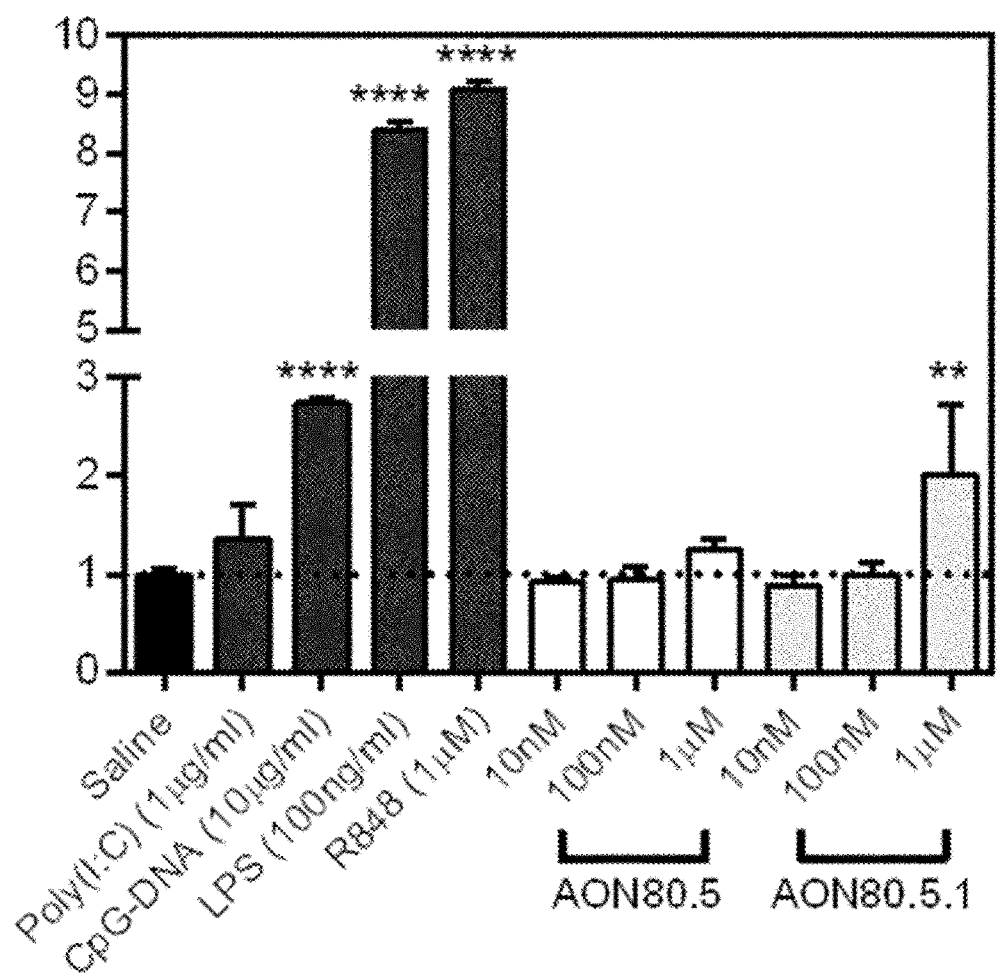
FIG. 6 shows immunogenicity (NF-κB and/or AP-1 activation) in response to the indicated treatments, including three doses for each of AON80.5 and AON80.5.1. The y-axis shows SEAP activity ($OD_{655nm}$ in arbitrary units), indicating the fold-change relative to saline. **$P<0.0001$, $P<0.01$, *$P<0.05$.

To assess the immunogenic effect of AONs the following in vitro experimental procedure can be followed, using the RAW-Blue cells of Invivogen. These RAW-Blue cells are derived from the murine RAW 264.7 macrophages and have an integrated secreted embryonic alkaline phosphatase (SEAP) reporter construct inducible by NF-κB and AP-1. The presence of agonists of all TLRs (with the exception of TLR5), NOD1, NOD2, RIG-I, MDA or DECTIN-1 induces signaling pathways leading to the activation of NF-κB and AP-1 and the subsequent production of SEAP. Levels of SEAP can be detected, thus indicating immunogenic activation. FIG. 6 shows the results of such testing after 24 hrs of in vitro stimulation. Positive controls CpG-DNA, LPS and R848 activated NF-κB and/or AP-1. In contrast, no activation of NF-κB and/or AP-1 was seen for the tested AON's compared to saline treated RAW-blue cells, except that AON80.5.1 induced a minor increase in SEAP at a final concentration of 1 μM, which might suggest activation of NF-κB and/or AP-1. Detected values were compared to saline using a One-Way ANOVA with Holm-Sidak test for multiple comparisons for SEAP (OD) measurements.

Immunotoxicity of AON's during 24 hrs of in vitro stimulation was also tested using RAW-Blue cells, looking for an increase in resorufin levels (which could be explained by increased proliferation leading to an increased cell number and/or by accelerated cell metabolism due to PPR activation). No effect on cell viability was observed after stimulation with any of the AON's (FIG. 7). Only the positive control CpG-DNA gave markedly elevated levels of synthesized resorufin (but the absence of an effect with LPS and R848 could be due to the use of old batches). Detected values were compared to saline using a One-Way ANOVA with Holm-Sidak test for multiple comparisons for resorufin measurements.

The functionality, e.g. protein stability and anchor fibril formation, of collagen VII without the exon 80 can be addressed using several in vitro methods described in literature:
 1. Protein analysis, both size and correct assembly of the α1-collagen chains, using western blotting (Titeux et al. 2010). Of note, due to the small size of the skipped exon and the large size of the wild type protein, the apparent difference in protein size may not be picked-up.
 2. Thermal stability analysis of the collagen VII homotrimer, by using western blotting under non-reduced conditions. Wild-type collagen VII is comprised of three α1-collagen a chains, and has a Tm of 41° C. (Mecklenbeck. 2002).
 3. Cell migration analysis using colloidal gold or scratch Radius™ 24-Well Cell Migration Assay. Compare the motility of fibroblasts and/or keratinocytes that express wild-type collagen VII vs the truncated protein without exon 80 (Chen et al. 2002). Or compare motility of keratinocytes in presence of treated vs non-treated mutant human fibroblast cell culture medium.
 4. Cell adhesion to various extracellular matrix components can be assessed, e.g. to collagen IV, laminin-332, laminin-1 or fibronectin (Chen et al. 2002).

The inventors of the present invention postulate that the AONs shown to perform the best in terms of preventing, or at least reducing, exon 80 inclusion into the mammalian (preferably human) COL7A1 mRNA will provide satisfactory results in terms of collagen VII functionality, as can be readily assessed using the above methods from the prior art.

It will be understood that the invention is described above by way of example only and modifications may be made whilst remaining within the scope and spirit of the invention.

REFERENCE LIST

Chen et al. Nat Genet. 2002, December; 32(4): 670-5. Restoration of type VII collagen expression and function in dystrophic epidermolysis bullosa.

Chiorini J A, Kim F, Yang L and Koting R M. J. of Virology 1999 February; 73(2):1309-19. Cloning and characterization of adeno-associated virus type 5.

Dorn A and Kippenberger. Mol Ther 2008. February; 10(1): 10-20. Clinical application of CpG-, non-CpG-, and antisense oligodeoxynucleotides as immunomodulators. Curr opin.

Egholm M et al. Nature 1993 Oct. 7; 365(6446): 566-8. PNA hybridizes to complementary oligonucleotides obeying the Watson-Crick hydrogen-bonding rules.

Fine et al., J. Am Acad Dermatol. 2014. June; 70(6):1103-26. Inherited epidermolysis bullosa: Updated recommendations on diagnosis and classification.

Goto M et al. J. Invest Dermatol. 2006. December; 126(12): 2614-20. Targeted Skipping of a Single Exon Harboring a Premature Termination Codon Mutation: Implications and Potential for Gene Correction Therapy for Selective Dystrophic Epidermolysis Bullosa Patients.

Govindaraju T and Kumar V A. Chem Commun (Camb) 2005 Jan. 28; (4):495-7. Backbone-extended pyrrolidine peptide nucleic acids (bepPNA): design, synthesis and DNA/RNA binding studies.

Keswani S G et al Wound Repair Regen. 2012. July-August; 20(4):592-600. Pseudotyped adeno-associated viral vector tropism and transduction efficiencies in murine wound healing.

Mecklenbeck Hum Gen Ther. 2002 Sep. 1; 13(13):1655-62. A microinjected COL7A1-PAC vector restores synthesis of intact procollagen VII in a dystrophic epidermolysis bullosa keratinocyte cell line.

Nielsen P E et al. Science 1991 Dec. 6; 254(5037):1497-500. Sequence-selective recognition of DNA by strand displacement with a thymine-substituted polyamide.

Titeux M. et al. Mol. Ther. 2010. August; 18(8):1509-1851N retroviral vectors expressing COL7A1 under human promoters for ex vivo gene therapy of recessive dystrophic epidermolysis bullosa.

The invention claimed is:

1. An antisense oligonucleotide (AON) capable of preventing or reducing exon 80 inclusion into a human COL7A1 mRNA when the mRNA is produced by splicing from a pre-mRNA in a cell, wherein the AON comprises a nucleotide sequence selected from SEQ ID NOs: 8, 25, 26, 31 and 32.

2. The AON of claim 1, wherein the AON comprises a region of complementarity with exon 80 wherein the region of complementarity is at most 20 nucleotides in length.

3. The AON of claim 1, wherein the AON is less than 24 nucleotides in length.

4. The AON of claim 1, wherein the AON is an oligoribonucleotide.

5. The AON of claim 1, wherein the internucleosidic linkages are chemically modified.

6. The AON of claim 1, wherein the AON comprises one or more lower 2'-O-alkyl substituted sugar moieties.

7. A method for preventing or reducing exon 80 inclusion into a human COL7A1 mRNA when the mRNA is produced by splicing from an RNA transcript in a human cell, the method comprising providing to (i) the cell, in vitro or ex vivo, (ii) a tissue comprising the cell, in vitro or ex vivo, or (iii) a living human being comprising the cell, the oligonucleotide of claim 1, under conditions conducive to uptake of the oligonucleotide by the cell, and allowing splicing to take place.

8. The AON of claim 2, wherein the AON comprises a region of complementarity with exon 80 that is 11, 12, 13, 14, 15, 16 or 17 nucleotides in length.

9. The AON of claim 3, wherein the AON is 20, 21, 22, or 23 nucleotides in length.

10. The AON of claim 5, wherein the internucleosidic linkages are phosphorothioate-linkages.

11. The AON of claim 6, wherein the lower 2'-O-alkyl substituted sugar moieties are 2'-O-methyl substituted sugar moieties.

12. A composition comprising the oligonucleotide of claim 1, and one or more of a carrier, excipient, stabilizer, transfection agent, diluent, gelling agent or buffer.

13. The AON of claim 1, wherein the AON consists of a nucleotide sequence selected from SEQ ID NOs: 8, 25, 26, 31 and 32.

14. The AON of claim 1, wherein the AON comprises one or more sugar moieties that comprise a substitution at one or two of the 2', 3' and 5' positions.

15. The AON of claim 14, wherein the substitution is selected from: -OH; -F; substituted or unsubstituted, linear or branched lower (C1-C10) alkyl, alkenyl, alkynyl, alkaryl, allyl, or aralkyl, that may be interrupted by one or more heteroatoms; O-, S-, or N-alkyl; O-, S-, or N-alkenyl; O-, S- or N-alkynyl; O-, S-, or N-allyl; O-alkyl-O-alkyl, -methoxy, -aminopropoxy; -methoxyethoxy; -dimethylaminooxyethoxy; and -dimethylaminoethoxyethoxy.

16. The AON of claim 1, wherein the AON comprises the nucleotide sequence of SEQ ID NO: 8.

17. The AON of claim 1, wherein the AON comprises the nucleotide sequence of SEQ ID NO: 25.

18. The AON of claim 1, wherein the AON comprises the nucleotide sequence of SEQ ID NO: 26.

19. The AON of claim 1, wherein the AON comprises the nucleotide sequence of SEQ ID NO: 31.

20. The AON of claim 1, wherein the AON comprises the nucleotide sequence of SEQ ID NO: 32.

* * * * *